United States Patent [19]

Kleinerman

[11] Patent Number: 5,004,913
[45] Date of Patent: Apr. 2, 1991

[54] REMOTE MEASUREMENT OF PHYSICAL VARIABLES WITH FIBER OPTIC SYSTEMS - METHODS, MATERIALS AND DEVICES

[76] Inventor: Marcos Kleinerman, 24 Jerome St., Southbridge, Mass. 01550

[21] Appl. No.: 711,062
[22] Filed: Mar. 12, 1985

Related U.S. Application Data

[63] Continuation-in-part of Ser. No. 608,932, May 14, 1984, Pat. No. 4,708,494, which is a continuation of Ser. No. 405,732, Aug. 6, 1982, abandoned.

[51] Int. Cl.⁵ .................... G01N 21/64; G01K 11/12; G02B 5/14; G01L 7/02
[52] U.S. Cl. .......................... 250/227.21; 250/227.23; 250/231.10; 250/458.1; 73/293; 73/714; 374/131; 374/161
[58] Field of Search .................. 250/227.21, 227.23; 73/714, 293

[56] References Cited

U.S. PATENT DOCUMENTS

| | | | |
|---|---|---|---|
| 3,239,406 | 3/1966 | Coffman et al. | 250/361 C X |
| 3,639,765 | 2/1972 | Kleinerman | 250/330 |
| 3,996,472 | 12/1976 | Rabatin | 250/337 X |
| 4,061,578 | 12/1977 | Kleinerman | 250/330 |
| 4,075,493 | 2/1978 | Wickershein | 374/159 |
| 4,111,050 | 9/1978 | Waddoups | 374/161 |
| 4,136,566 | 1/1979 | Christensen | 250/227 X |
| 4,215,275 | 7/1980 | Wickersheim | 374/137 |
| 4,223,226 | 9/1980 | Quick et al. | 250/458 |
| 4,245,507 | 1/1981 | Samulski | 356/44 X |
| 4,262,198 | 4/1981 | Gupta et al. | 250/340 |
| 4,278,349 | 7/1981 | Sander | 356/44 |
| 4,281,245 | 7/1981 | Brogardh et al. | 250/227 |
| 4,302,970 | 12/1981 | Snitzer et al. | 374/161 |
| 4,307,607 | 12/1981 | Saaski et al. | 374/161 |
| 4,313,057 | 1/1982 | Gelbwachs | 250/458.1 |
| 4,327,963 | 5/1982 | Khoe et al. | 374/131 X |
| 4,342,907 | 8/1982 | Macedo et al. | 374/131 X |
| 4,356,448 | 10/1982 | Brogardh et al. | 250/231 R X |
| 4,374,328 | 2/1983 | Tekippe et al. | 374/121 X |
| 4,376,890 | 3/1983 | Engström et al. | 250/231 R X |
| 4,409,476 | 10/1983 | Löfgren et al. | 250/337 X |
| 4,437,772 | 3/1984 | Samulski | 374/129 |
| 4,443,699 | 4/1984 | Keller | 250/227 |
| 4,443,700 | 4/1984 | Macedo et al. | 250/227 |
| 4,448,547 | 5/1984 | Wickersheim | 374/131 X |
| 4,451,730 | 5/1984 | Brogardh et al. | 73/800 X |
| 4,462,699 | 7/1984 | Shaw et al. | 374/131 |
| 4,523,092 | 6/1985 | Nelson | 250/226 |
| 4,539,473 | 9/1985 | Brogardh et al. | 73/777 X |
| 4,562,348 | 12/1985 | Brogardh et al. | 250/231 P X |
| 4,576,486 | 3/1986 | Dils | 250/339 X |
| 4,880,972 | 11/1989 | Brogardh et al. | 250/231 R |

FOREIGN PATENT DOCUMENTS 2064107  6/1981  United Kingdom ................ 374/130

OTHER PUBLICATIONS

"Optical Fibers with Reduced Pressure Sensitivity", N. Lagakos et al., May 5, 1981, Optics Letters, vol. 6, No. 9, Sep. 1981, pp. 443-445.

"A Temperature Measuring Device", E. Okamoto et al., Feb. 21, 1974, Early Patent Application, 51452/72, pp. 3-8.

Introduction to Solid State Physics, by Charles Kittle, Nov. 1957, pp. 495, 496, 516, 517, 524.

McGraw-Hill Dictionary of Scientific and Technical Terminology, ©1978, p. 948, "Luminescent Center" defined.

Primary Examiner—Daniel M. Yasich
Attorney, Agent, or Firm—Stanley J. Yavner

[57] ABSTRACT

Methods, materials and devices for the remote measurement of physical variables with fiber optic systems use a single excitation light source for generating through the use of at least one luminescence converter, both a signal beam and a reference beam, and allow the transmission of both beams through a single fiber to a single photodetector, thus producing photo-electric signals the relative intensities of which are only minimally affected by changes of the intensity of the interrogating light beam, optical losses, or detector drift. In contrast to the prior art, the luminescent materials of this invention can be used either as transducers for physical parameters or as means for processing information from other optical transducers, without requiring a change in the luminescence properties of said materials under the influence of the measured parameter. Furthermore, the techniques and devices of this invention allow the use of luminescent materials for converting a measurand with a low coefficient of change under the action of the parameter being measured into a measurand with a large coefficient of change.

28 Claims, 19 Drawing Sheets

REMOTE MEASUREMENT OF PHYSICAL VARIABLES WITH FIBER OPTIC SYSTEMS - METHODS, MATERIALS AND DEVICES

CROSS-REFERENCE TO RELATED APPLICATIONS

This is a continuation-in-part of copending patent application Ser. No. 608,932, filed May 14, 1984, now U.S. Pat. No. 4,708,494, which is in turn a continuation of application Ser. No. 405,732, now abandoned, and is also based in part on the disclosure subject of the disclosure document No. 114,924, filed on Feb. 16, 1983.

BACKGROUND OF THE INVENTION

The present invention relates to improved methods and devices for the remote measurement of physical variables with multimode fiber optic systems, and more particularly is directed to the novel use of luminescence techniques for increasing the accuracy of remote fiber optic measurements.

DESCRIPTION OF THE PRIOR ART

Fiber optic sensing systems have been under development in recent years for the remote measurement of physical variables which can be made to generate optical signals. There are two main approaches to fiber optic sensing, as follows:

(a) The use of the fiber itself as the transducer, in a system which may be interferometric or non-interferometric, and (b) The use of a point transducer attached or otherwise optically connected to one or more optical fibers, the latter acting merely as light guides.

These and other approaches are discussed in a recent review by Giallorenzi et al, *IEEE Journal of Quantum Electronics,* v. QE-18, No. 4, Apr. 1982.

Interferometric sensing systems use the fibers themselves as transducers, and can achieve very high sensitivities. They have, however, several disadvantages. They usually require single mode lasers, single mode fibers, and relatively complex instruments, and are often subject to drift and phase noise due to environmental factors other than the measured variables. Also, they are not at present compatible with the industrial requirements for ruggedness. Non-interferometric systems using multimode fibers are simpler, more rugged and are capable of meeting most of the sensitivity requirements of industry. The methods and devices of this invention utilize these systems.

In order to obtain a reliable measurement of a physical variable with a fiber optic system, it is necessary to compare the optical signal generated by the variable to a reference signal which is unaffected by the variable. This is commonly done by splitting the interrogating light beam into two beams, each carried by a different fiber. One of these beams is made to interrogate the variable being measured, resulting in a change of a property of said beam, like its intensity. The beam thus modified is sent to a photo-detector at a (usually remote) measuring station. The reference beam is sent to a second photo-detector at the same measuring station. The intensity ratio of these two beams is a known function of the measured variable. For the measurement to be accurate, it is necessary that the photo-detectors have a very stable response. This requirement is not always met, as detector response tends to drift somewhat with time, and is also subject to some degree of temperature drift. This introduces an error in the measurement. Another source of error is unequal transmission loss in the two fibers. This can occur if the fibers are long and/or are subject to non-identical stresses or other influences.

In another ratio method, two light beams of different wavelengths are transmitted through the same fiber system. Only one of these two beams is modified by the measured variable. Both beams are then sent by the same fiber to the measuring station. There are two ways to accomplish this. One way is to carry both beams simultaneously, and then to separate them at the fiber output by means of wavelength-selective filters, feeding each separated beam to a different photo-detector. The other way is to use a switching device to send both beams alternately through the same fiber system to the same photo-detector. The latter method was used to measure temperature by monitoring the temperature-dependent transmission of light in semiconductors within their absorption band edge (Kyuma et al., *IEEE J. Quant. Electron.*, QE-18(4), 677 (1982)). Each of these methods is subject to error, due either to unequal detector drift or to non-identical fluctuations of the intensities of the two light beams. Furthermore, these techniques cannot be used with optical sensing methods which do not have a large degree of wavelenth selectivity.

In yet other methods, luminescent materials have been used to a limited extent for the measurement of temperatures and high pressures with optical systems, but their use required a change in their luminescence spectral distribution, quantum efficiency or decay time. Thus, temperature has been measured by its effect on the luminescence intensity ratio of two spectral bands in the luminescence from suitable phosphors (U.S. Pat. Nos. 3,639,765; 4,061,578; 4,075,493; and 4,255,275) and from the temperature-dependent luminescence decay time from a few other phosphors (U.S. Pat. Nos. 4,245,507 and 4,437,772). High pressures can be measured by their effect on the luminescence intensity ratio of two spectral bands in ruby (*Scientific American*, Apr. 1984, page 57). Only a relatively small number of efficient luminescent materials exhibit such changes to the extent required for high sensitivity and accuracy.

Accordingly, it is an object of the invention to develop methods and devices which eliminate or minimize the sources of error discussed above by producing both a signal beam and a reference beam from a single light source, whether this be a broad band or a narrow band or monochromatic source, carrying both beams simultaneously through a single fiber to a single photo-detector, and separating, measuring and ratioing both photoelectric signals by simple means.

Another source of error in known fiber optic sensor systems occurs in the use of attenuation measurements for the estimation of a physical variable. Many actual or proposed sensors are based on deformation of a clad optical fiber by the physical variable being measured. This deformation couples light out of the fiber core modes into the cladding. The attenuation of the core modes is used as a measure of the physical variable. This method, usually called "bright mode sensing" is subject to appreciable noise, especially when long fibers are needed to carry the attenuated beam, because Rayleigh scattering and other mechanical disturbances along the fiber length also attenuate the core light. In order to minimize noise from these sources, at least one system has been devised for measuring directly the light coupled into the cladding by the measured variables (Lagakos et al., *Applied Optics*, 20, 167 (1981)). But this method, including the extraction of the cladding light at or near the sensor location, is relatively complicated for use at long sensor-to-instrument distances. Another disadvantage of "bright mode sensing" is that variables which produce small signals must be estimated indirectly from a difference between two large, relatively noisy signals. This is similar to measuring real absorption of light by transmission measurements. It is well known that such measurements cannot be made with a high degree of accuracy when the optical density is of the order of magnitude of $10^{-3}$ or lower. There is a need, therefore, for a simple method for measuring directly and accurately small fractions of light coupled out of the fiber core into the cladding. This method must be capable of implementation at long fiber-to-instrument distances and be immune to fluctuations of the intensity of the interrogating light beam, fiber and/or connector losses and detector drift.

It is, therefore, another object of the present invention to provide such a method, which employs luminescent materials, together with devices for its implementation.

Yet another object of the present invention is to provide new methods and devices for improving the accuracy of measurements of small changes in intensity of an interrogating light beam as it interacts with the physical variable being measured with a fiber optic system.

Still another object of the present invention is to provide new methods and devices for the measurement of diverse physical variables at a plurality of remote locations simultaneously or quasi-simultaneously, using a single excitation light source and a single photo-detector, with the different sensors attached along an input optical bus, said measurements being only minimally affected by intensity fluctuations of the interrogating light beam, fiber losses, connector losses or detector drift.

Other objects of the present invention will in part be apparent from the following discussion and will in part appear hereinafter.

SUMMARY OF THE INVENTION

This application is a continuation-in-part of application Ser. No. 608,932 filed May 14, 1984, now U.S. Pat. No. 4,708,494, which in turn is a continuation of application Ser. No. 405,732 filed Aug. 6, 1982, now abandoned. The claimed invention is an extension of the teachings of said patent, the claims of which were restricted to temperature measuring technology, into an invention for the sensing and/or measurement of diverse physical variables including, besides temperature, any physical parameters which can cause a variable attenuation of light propagating *inside* an optical probe. The probes used in this invention have the common property of modulating the interrogating light and generating an optical signal in the form of a light separable from the interrogating light, at least part of the intensity of which is emitted from the probe at wavelengths different from the wavelength or wavelengths of the interrogating light. A preferred class of probes are photoluminescent probes, and these are used in a manner which permits the ratiometric measurement of any physical variable which can be made to affect the intensity of a light beam propagating therein. As used in the present invention, photoluminescent probes serve either as transducers for the physical variable or as modifiers or conditioners of a signal from another transducer or that from the interrogating light beam used as a reference. This is made possible by the following characteristics of photoluminescent materials (and other wavelength converting materials):

(1) A photoluminescent material excited by an interrogating light beam is an optically powered light source with a wavelength and/or time domain characteristic different from those of the interrogating beam, but with an intensity which is directly proportional to that of the interrogating beam. With a photoluminescent probe one can thus generate a set of two light beams: a signal beam and a reference beam, both of which can travel through the same optical fiber simultaneously to one photodetection station, where they are separated and ratioed to give a reading only minimally affected by fluctuations of the intensity of the interrogating light beam, fiber and/or connector losses or detector drift.

(2) In systems where the sensed or measured variable attenuates the intensity of the interrogating light beam inside an optical probe, a photoluminescent material can convert a small attenuation—which would otherwise have to be determined *indirectly*—from a small difference between two large signals—into an essentially zero background, *direct signal*, separated spectrally and/or temporally from the interrogating light beam. This increases the sensitivity and the accuracy of the measurement. Some fiber optic thermometers described in this specification are one example. Another example are the sensor systems based on core/cladding light redistribution wherein the light deflected from the fiber core to the fiber cladding is converted into luminescence light having wavelengths different from those of the interrogating light.

(3) By introducing new light propagation modes in an optical fiber system, a photoluminescent material permits the construction of devices not easily realizable otherwise. For example, a single photoluminescent fiber can be used for measuring continuous liquid level changes with instrumentation not much more complex than that used with "on/off" liquid level indicators, as described hereinafter in the specification.

Because this specification can support a plurality of divisional applications, the claims of this application are selectively drawn to systems where the physical variable being sensed or measured attenuates the intensity of the interrogating light *inside* a probe for the physical variable (parameter), from an initial intensity $P_o$ injected *into* the wavelength-converting probe to the attenuated intensity $P_o(1-\alpha)$, where $\alpha$ is a fraction the value of which varies as a function of the magnitude of the physical parameter. The fraction $\alpha P_o$ of the intensity of the interrogating light which is removed from the probe under the action of the physical variable—and lost or otherwise discarded in the techniques of the prior art—is converted, according to the teachings of this invention, into a light at least part of the intensity of which is emitted at wavelengths different from the wavelength or wavelengths of the interrogating light, and with an intensity which is substantially proportional to the value of $\alpha$. The fraction $\alpha$ can be, for example, the fraction $\alpha_v$ of the intensity of the interrogating light which is absorbed within a photoluminescent temperature probe, as discussed in section B and illustrated in FIG. 5. It can also be the fraction $\alpha$ of the intensity of the interrogating light injected into the core of an optical fiber which is deflected from the core to the fiber cladding, as discussed in section C.

Since the usefulness of photoluminescent materials for the practice of this invention does not require any change in the photoluminescence properties under the influence of the measured variable, virtually all photoluminescent materials having a relatively high luminescence quantum yield are useful as probes for this invention.

The invention is particularly useful for the sensing and/or measurement of values of $\alpha$ much smaller than 0.10, and for the measurement of physical parameters at several or numerous locations using a single, continuous optical fiber probe. The improvements of this invention over the prior art should be easily appreciated from the following example:

Suppose that one is measuring a physical parameter by interrogating a light-transmissive probe for the parameter. The parameter produces an attenuation of light transmitted by the probe proportional to the magnitude of the parameter. Under the action of the parameter the interrogating light entering the probe with an intensity $P_o$ is attenuated by a fraction $\alpha P_o$ of one percent of its original intensity, that is to an intensity of $0.9900P_o$, the value of $\alpha$ being equal to 0.01. It is necessary to measure the parameter to an accuracy of one percent. Since the attenuation is proportional to the magnitude of the parameter, an increase of one percent in this magnitude will increase the value of $\alpha$ by one percent, to 0.0101, and decrease the intensity of the transmitted light to $0.9899P_o$. With prior art techniques one would have to estimate the change in the value of $\alpha$ *indirectly*, by measuring first the intensity of the light transmitted by the probe, that is $0.9900P_o$, and then $0.9899P_o$. This is a difference of one part in 10,000, which is not readily measurable with most industrial gages. And even if industrial gages could measure this difference accurately, the measurement would not be valid unless the intensity of the interrogating light itself could be held constant to better than one part in 10,000, which is difficult. If, for example, the stability of the light source were as good as one part per thousand, the measurement of the parameter would have an unacceptably high error of *10 percent*, even with a perfect gage.

If, however, the otherwise lost fraction of the intensity of the interrogating light (that is, $\alpha P_o$) is converted into light emitted from the probe at wavelengths different from those of the interrogating light, for instance by a photoluminescent converter, it can be entirely separated from the injected and transmitted interrogating lights and measured *directly*. The measured intensity of the converted light will be proportional to the value of $\alpha$, *not* $(1-\alpha)$, and a change of one percent in the value of $\alpha$ will change the intensity of the measured luminescence light by 1.0 percent, *not* 0.01 percent like the change in the value of $(1-\alpha)$. The measurement of the physical parameter is then much more accurate and can be carried out with relatively inexpensive instruments, because the accuracy of the light intensity measurements needed to measure the physical variable (parameter) to within one percent of its magnitude is now one part per hundred (one percent) instead of one part per 10,000 (0.01 percent).

DEFINITIONS

Within the context of this application, I am using the following definitions:

Light: optical radiation, whether or not visible, which is absorbed, emitted and/or otherwise modified by an optical sensor or device.

Occupancy number of an energy level: the fraction of the molecules of a material occupying said energy level.

Vibronic material: any material whose molecular electronic energy ground level comprises a plurality of vibrational sublevels with energies higher than that of the lowest occupied level of the material, said vibrational sublevels being so distributed as to cover an essentially continuous wide band of energies.

Vibronic level: a vibrational level of the electronic ground state of a vibronic material, having an occupancy number which increases with increasing temperature according to the Boltzmann distribution function.

Physical variable: any physical property which can change in value. Examples: temperature, pressure, flow rate, liquid level, position, and the like.

Physical parameter: physical variable

Force: any action which affects the transmission of light along an optical fiber. Examples: stress, pressure, sound waves, and the like.

Interrogating light: illuminating light directed to a sensor for a physical variable (physical parameter).

Excitation light: illuminating light.

Light beam: light being propagated through the optical system, including optical fibers, regardless of degree of divergence.

DETAILED DESCRIPTION OF THE INVENTION

Figure 1:
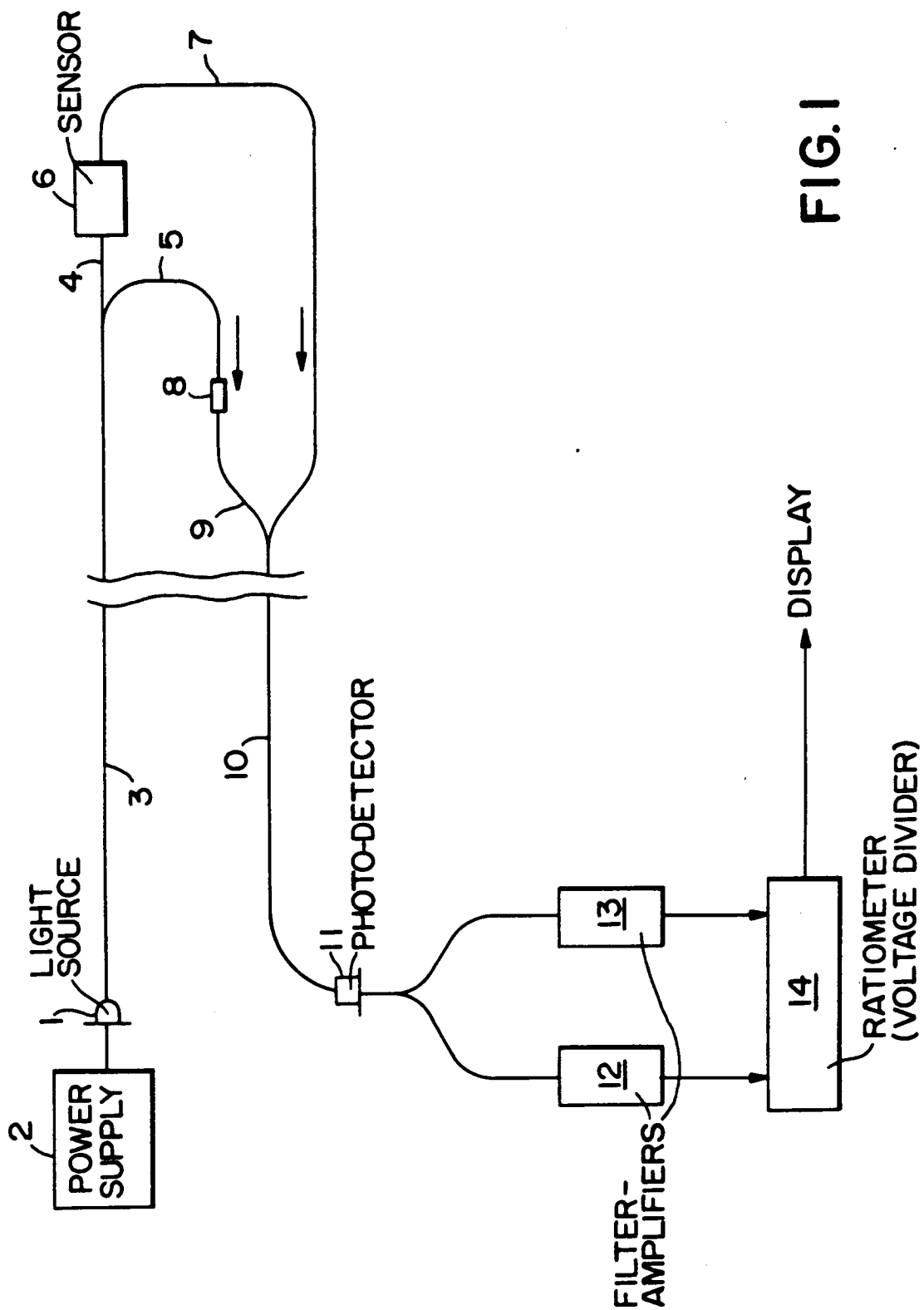
FIG. 1 is a schematic representative of one of the basic embodiments of this invention.

A. General Ratio Method for Measuring Physical Variables with Fiber Optic Systems FIG. 1 is a schematic representation of an embodiment of this invention which allows both the signal beam produced by the measured variable and a reference beam to be carried by the same fiber to a single detector. A light source 1 consisting of a light-emitting diode (LED) or a diode laser is driven by power supply 2 to produce a light beam consisting of a train of regularly recurring light pulses with a decay time $\tau_1$ of about $10^{-6}$ seconds or shorter. Said light beam, hereinafter referred to as the interrogating light beam, is launched into optical fiber 3, which carries the beam to the sensor. Prior to reaching the sensor, fiber 3 is split into two branches, 4 and 5. Branch 4 carries a known fraction of the intensity of the interrogating light beam to sensor 6, said sensor interacting with the physical variable being measured as will be discussed in detail below. The interaction produces a light beam made of pulses having an intensity or polarization related in a known manner to the measured variable, but with the value of $\tau_1$ remaining unchanged. This beam is launched into fiber segment 7.

Branch 5 carries a known fraction of the intensity of the interrogating light beam to a luminescence converter 8, wherein the incident light pulses are converted to luminescence pulses with a decay time $\tau_2$ much longer than $\tau_1$, and a wavelength different from that of the incident beam, said luminescence pulses being fed to fiber segment 9. Fiber segments 7 and 9 are then joined into fiber 10, through which both the light beam emerging from the sensor and the luminescence beam produced by converter 8 are fed to photo-detector 11. The photo-electric signals generated therein by the two beams are separated and amplified by the filter-amplifiers 12 and 13, which are tuned to decay times $\tau_1$ and $\tau_2$, respectively. The amplified electrical signals are ratioed by ratiometer 14. The measured ratio is a known function of the measured variable, essentially independent of fluctuations of the intensity of the interrogating light beam, fiber and/or connector losses, or detector drift.

Examples of sensors which can be used with the general embodiment of FIG. 1 are given below.

EXAMPLE 1.

Sensor 6 is a pressure gauge made of a polyurethane photo-elastic material placed between two crossed polarizers. In the absence of an applied pressure the system is opaque to the light carried to it by fiber segment 4. An applied pressure induces a stress on the sensor, resulting in light being transmitted through the sensor to fiber segment 7. The interrogating light beam has a wavelength of 807 nanometers (nm), and the luminescent converter 8 is a short length of a phosphate glass fiber having a concentration of $Nd^{3+}$ ions sufficiently high to absorb virtually all the 807 nm light incident on it. The $Nd^{3+}$ ions emit luminescence, most of which within two spectral bands peaking near 880 and 1060 nm, respectively, and with a decay time longer than $10^{-4}$ seconds.

EXAMPLE 2.

The sensor is a temperature transducer consisting of a layer of the semiconductor (Al)GaAs, having a temperature-dependent absorption edge wavelength region including the light source wavelength of 807 nm. The luminescence converter is a $Nd^{3+}$ glass fiber as in Example 1. The intensity of the light transmitted by the semiconductor, divided by the luminescence intensity produced by the converter, is a known function of temperature.

It should be apparent to persons with ordinary skill in the art to which this invention pertains that the luminescence converter 8 can be attached to fiber segment 7 instead of fiber segment 5, and the ratiometric feature would operate in the same manner as described above.

Figure 2:
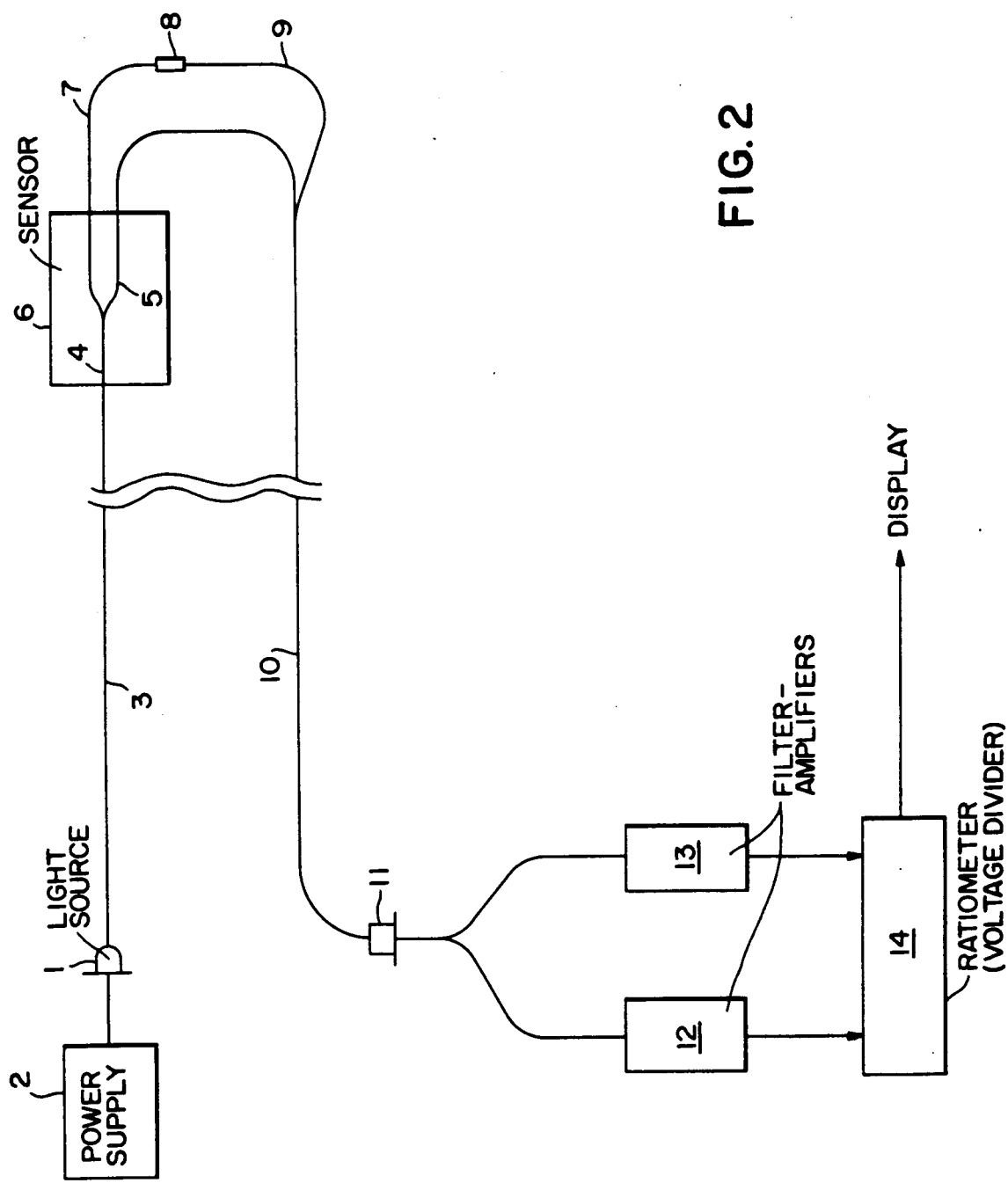
FIG. 2 is a variation on the embodiment of FIG. 1.

A variation of the general method illustrated in FIG. 1 is shown in FIG. 2. It differs from that of FIG. 1 in that the parameter being measured causes a redistribution of light between fibers 4 and 5 at the point of coupling, wherein the extent of light redistribution is a function of the physical parameter being measured.

EXAMPLE 3.

Figure 3:
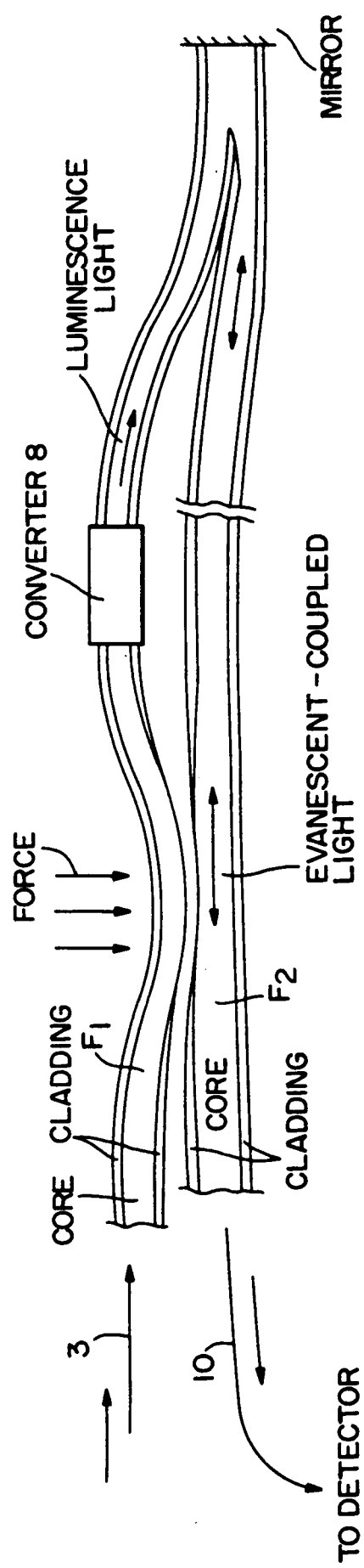
FIG. 3 illustrates a displacement transducer based on the invention.

Sensor 6 of FIG. 2 is an evanescent wave coupler as illustrated in FIG. 3. Light launched into the core of fiber F1 is partially coupled to the core of fiber F2, the extent of coupling being determined by the distance between the fiber cores. Fiber F2 is in a fixed, rigid position, whereas fiber F1 can be moved relative to fiber F2 by an applied pressure, the value of which determines the distance between said fiber cores and, hence, the extent of light redistribution between them. According to the invention, the fraction of the light in fiber F1 which is not coupled into fiber F2 is converted into a luminescence light within a wavelength region $\lambda_1$ different from that of the interrogating light beam. The luminescence converter 8 is in this case a short segment of Neodymium-doped glass fiber. This luminescence light can be joined to the light coupled into fiber F2 of FIG. 3, and both light beams can be carried by a single fiber, simultaneously, to a single photodetector according to the general method described hereinbefore.

EXAMPLE 4.

Figure 4:
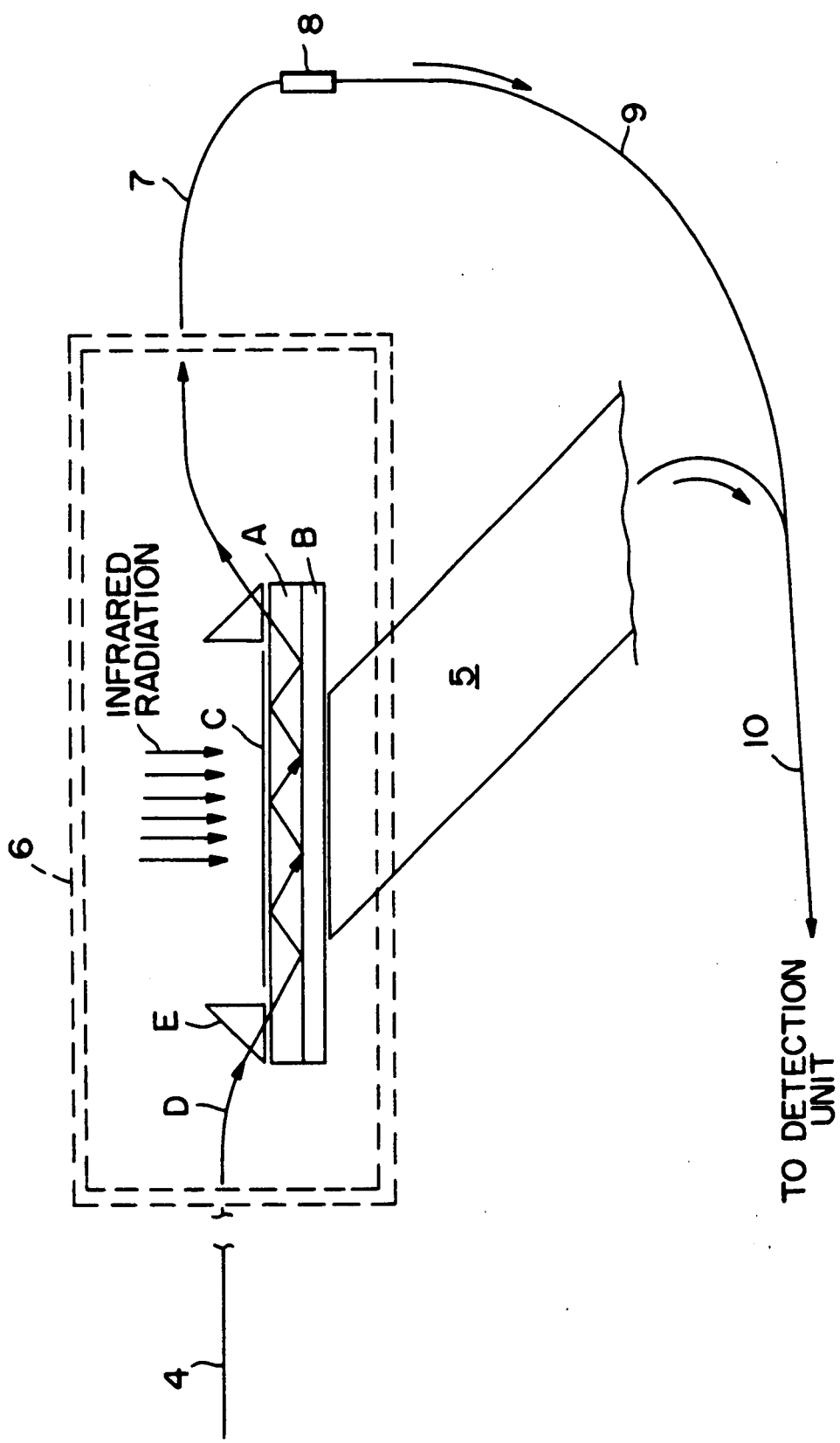
FIG. 4 illustrates an infrared radiometer based on the invention.

Another embodiment of this invention is a remote infrared radiometer as described below, based on the decrease of the refractive index of a thin fiber waveguide produced by the heating effect of the absorbed infrared radiation being measured. The process is illustrated by FIG. 4, where the dotted box represents sensor 6 in FIG. 2.

The thin film waveguide A, about two micrometers thick and made from a material having an index of refraction $n_w$ with a relatively large temperature coefficient, is in optical contact on one side with a transparent substrate B having a refractive index $n_s$ lower than $n_w$.

On its other surface the waveguide has a thin reflecting metallic coating C with a thickness of the order of $10^{-6}$ to $10^{-5}$ cm. This metallic film acts also as an absorber for the incident infrared radiation being measured. A light beam D from a diode laser is coupled to the waveguide by means of a miniature prism E. The beam travels along the waveguide, propagated by Total Internal Reflection, and with a number of angular modes which depends on the ratio $(n_w/n_s)$. When infrared radiation is absorbed by the metallic coating C, the heating effect on the waveguide decreases the value of $n_w$ and causes a fraction of the intensity of the interrogating light beam comprising the higher angular modes to be deflected out of the waveguide into substrate B and then to optical fiber 5, which carries the deflected light to a photodetector. The fraction of the intensity of the interrogating light beam which is coupled to fiber 5 is related to the intensity of the incident infrared radiation. Both the diode laser and the photodetector can be at a remote location from the sensor waveguide, and connected to it by fiber optic links.

In a practical system one should AC-modulate the incident infrared radiation at a fixed, narrow bandwidth frequency, and measure the signal with a filter/amplifier tuned to said AC frequency, in order to be able to measure weak signals in the presence of wide band noise.

B. The Measurement of Temperature

Virtually all efficient luminescent materials can be used according to the teachings of this invention for the ratiometric measurement of temperatures over a wide temperature range. In the general method described in detail below, a luminescence intensity excited in the spectral region where the material has a temperature-dependent absorption coefficient is used for the *direct* measurement of the temperature-dependent absorption and, hence, of the temperature of the object or environment around said material. The method is illustrated with reference to FIG. 5, which represents a molecular energy level diagram of the luminescent centers of a typical vibronic luminescent material and their temperature-dependent absorption and luminescence properties. Such a material will be termed hereinafter a vibronic material.

Figure 5:
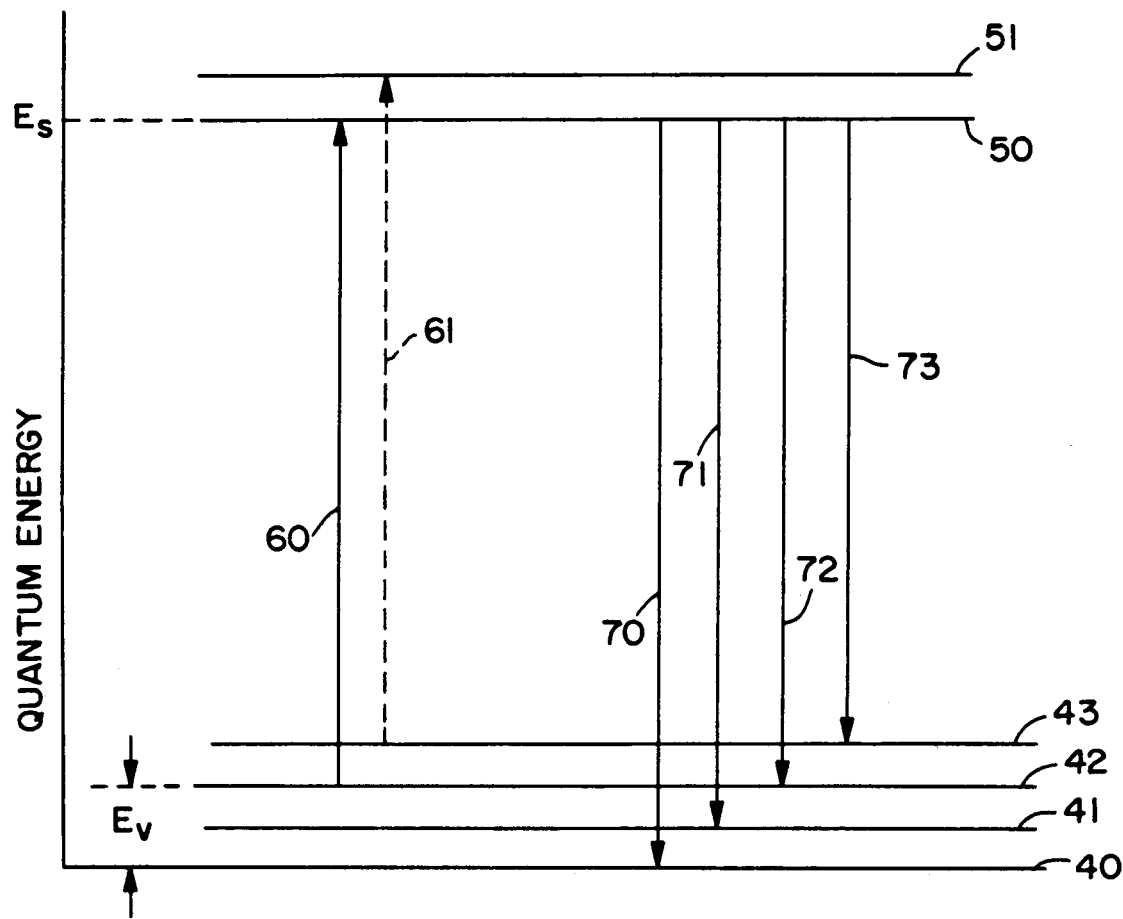
FIG. 5 shows an energy flow sheet, at the molecular level, of a luminescent material useful for measuring temperature according to the invention.

Referring to FIG. 5, the ground electronic level of the luminescent centers comprises vibrational sublevels 40, 41, 42, 43 and other levels which, for the sake of simplicity, are not shown. The excited electronic level comprises vibrational sublevels 50, 51 and other levels not shown. The vertical arrowed line 60 represents an electronic transition, produced by the absorbed excitation light, from vibrational sublevel 42 to level 50, the lowest vibrational sublevel of the excited electronic level. The length of line 60 corresponds to the photon energy of the transition and, hence, to a specific wavelength of the excitation light. Said wavelength can excite only molecules occupying vibrational level 42 and, to a smaller extent, molecules occupying slightly higher levels, the excitation of which is represented by the dotted vertical line 61. Luminescence emission occurs from level 50 to the vibrational levels of the ground electronic level, said emission represented by lines 70, 71 72 and 73. As shown in the figure, a considerable spectral portion of the emission occurs at photon energies higher than that of the excitatiom light, and is commonly referred to as anti-Stokes luminescence. The emitted photons can have a higher energy than the excitation photons because the optically excited molecules had, in addition to the energy of the excitation photons, the vibrational energy $E_v$ of vibrational level 42.

In practice the vibronic material is often used as a liquid, glassy or crystalline solution in a transparent host material, said solution constituting the temperature sensor. The concentration of the vibronic material and the dimensions of the sensor are chosen so that the sensor absorbs only part of the nearly monochromatic excitation light within the temperature range of operation, and transmits the rest. The absorbed fraction $a_v$ of the incident excitation light follows the relation $$a_v = 1 - 10^{-\epsilon' c_o d(N_{42}/N)} \qquad \ldots B1$$

where $\epsilon'$ is the molar decadic absorption coefficient of the molecules occupying vibronic level 42;

$c_o$ is the total molar concentration of the luminescent centers of the vibronic material;

d is the length of the sample in the direction of the incident illumination light;

$N_{42}$ is the number of luminescent centers of the vibronic material occupying vibronic level 42; and N is the total number of luminescent centers of the vibronic material. The ratio $(N_{42}/N)$ essentially follows the relation $$N_{42}/N = f^{-1} \exp(-E_v/kT) \qquad \ldots B2$$

where f is the partition function of the luminescent molecular system;

k is the Boltzmann constant; and

T is the absolute temperature in kelvins.

The expression $c_o f^{-1} \exp(-E_v/kT)$ is essentially the effective molar concentration of the luminescent centers occupying vibronic level 42.

Equations B1 and B2 are generally valid at any optical density, whether high, low or intermediate. In any case the luminescence intensity is essentially proportional to $P_o a_v$, where $P_o$ is the radiant power of the illuminating light *incident* on the sensor. A measurement of the generated luminescence intensity is, therefore, a *direct* measurement of absorption. The intensity of the light transmitted through the sensor is, in the abscence of scattering, proportional to $P_o(1 - a_v)$. Therefore, by measuring the ratio of the luminescence intensity to the transmitted light intensity one is effectively measuring the ratio $a_v/(1 - a_v)$, which is essentially independent of fluctuations of the intensity of the interrogating light beam or of light losses in the optical system.

At optical densities no greater than about 0.02, $a_v$ is essentially given by the equation $$a_v = 2.3 c_o \cdot d \cdot f^{-1} \exp(-E_v/kT) \qquad B3$$

The luminescence intensity I obeys the relation $$I = P_o(\lambda_o/hc) a_v \phi \text{ photons} \cdot \text{sec}^{-1} \qquad B4$$

where $\lambda_o$ is the wavelength of the excitation (illumination) light, h is Planck's constant, $\phi$ is the luminescence quantum efficiency of the sensor material, and c is the velocity of light in a vacuum.

Used with materials having high $\phi$ values, the system for measuring temperatures herein disclosed can produce large signal-to-noise ratios even with optical densities lower than 0.01, provided that the optical system has at least a moderately high collection efficiency for the generated luminescence. Such efficiency is easily obtainable with state-of-the-art fiber optics systems. When the fraction $a_v$ is of the order of one percent or less throughout the measured temperature range, the intensity of the transmitted light stays approximately constant.

The temperature coefficient of the luminescence intensity follows approximately the relation $$(1/I_o)(dI/dT) = E_v/kT^2 \qquad \ldots B5$$

where $I_o$ is the intensity at a chosen reference temperature. For example, a material with an $E_v$ value of 1800 cm$^{-1}$ has a coefficient close to three percent per kelvin at a temperature of 295K.

The intensity ratio R of the light emitted to the light transmitted by the luminescent material is independent of the intensity of the interrogating light beam, fiber and/or connector losses or detector drift.

Figure 6:
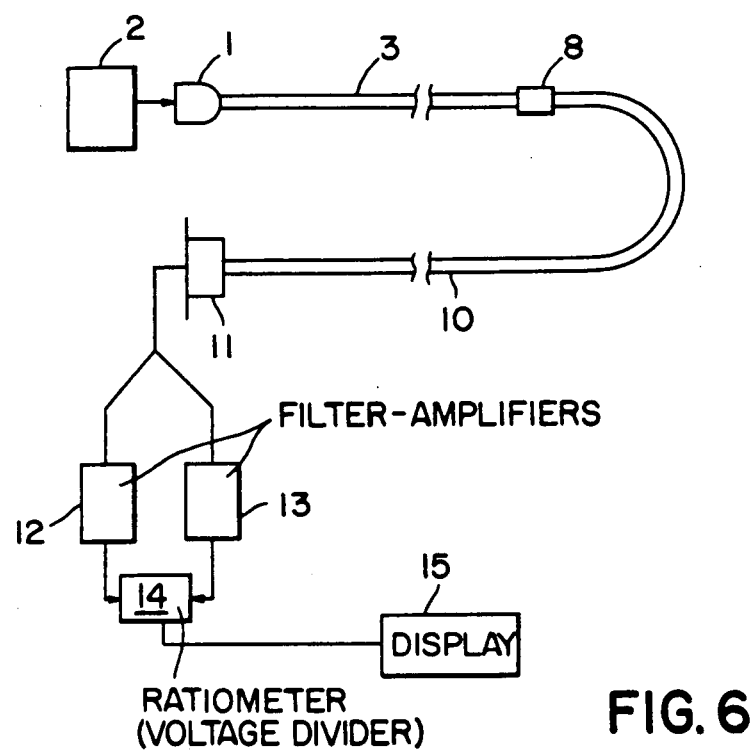
FIG. 6 illustrates an embodiment of a thermometer according to the invention.

A simple device for the optical measurement of temperature according to the methods of this invention is shown schematically in FIG. 6 wherein the temperature sensor 8 consists of one of the luminescent materials disclosed herein, the absorption coefficient of which varies as a known function of temperature when excited with light within a specific spectral region, and the luminescent centers of which have a luminescence decay time $\tau$ of the order of $10^{-5}$ seconds, or longer. Sensor 8 is illuminated with light within said defined spectral region from a source 1, preferably, but not limited to a light-emitting diode (LED) or a diode laser. Said light source is pulsed or AC-modulated by the power supply 2, so that the light intensity decays repetitively in a time much shorter than $\tau$. The excitation light from source 1 is directed to sensor 8 via the fiber optics light guide 3. The excitation light transmitted by, and the luminescence light emitted by sensor 8 are both carried, via the fiber optics light guide 10, to photodetector 11, and the electrical signals generated therein are separated by the electrical frequency filters 12 and 13. Filter 12 transmits the electrical signal from said excitation light, whereas filter 13 transmits the electrical signal from said sensor luminescence. The ratio of these signals, measured by the electronic divider 14, is an indication of the sensor temperature, which is displayed on the display device 15. A similar device can be used when the sensor contains two kinds of luminescent centers the decay times of which are very different from each other.

A parallel arrangement of electrical frequency filters is useful for measuring a temperature-dependent luminescence decay time. The filters are tuned, respectively, to the time frequencies corresponding to the upper and lower limits of the decay time within the temperature range of operation of the device. The relative fractions of the electrical signals transmitted by the filters is an indication of the luminescence decay time and, hence, of the sensor temperature. Thus, by adding another electrical frequency filter to the device shown in FIG. 6 one can measure both the temperature-dependent light absorption and luminescence intensity of a sensor and its temperature-dependent luminescence decay time. Since both parameters can be operationally independent of each other, such a simple device can check its own accuracy by comparing readings obtained from both measurements. As an alternative, and depending on the particular configuration appropriate to the system being measured, one can use the intensity ratio of the luminescence light to the illuminating light incident on the sensor as an accurate temperature indicator.

Figure 7:
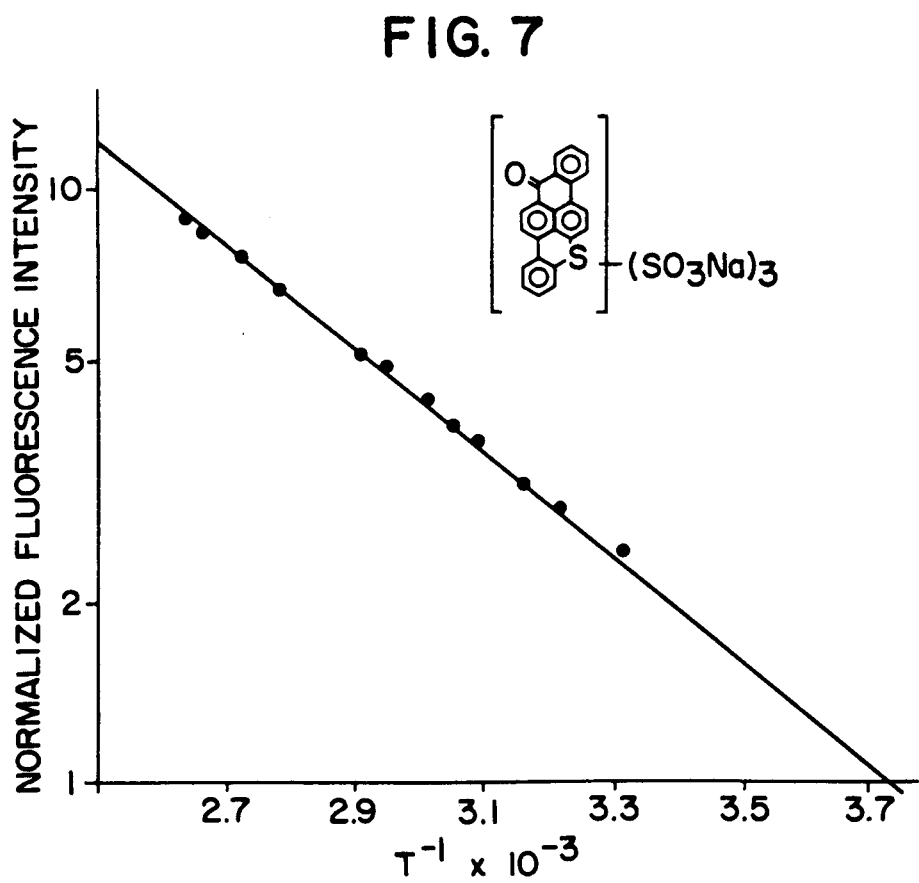
FIG. 7 is a graph of the temperature dependence of the normalized fluorescence intensity of a temperature sensor used according to this invention.

FIG. 7 shows *actual* normalized fluorescence intensity versus inverse *absolute* temperature of a dimethyl sulfoxide (DMSO) solution of the dye represented by the formula

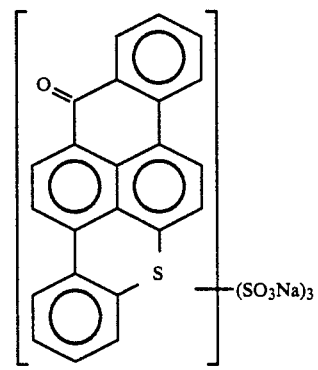

illuminated by a light beam from a helium-neon laser. The dye concentration was approximately $10^{-4}$ Molar. The fluorescence intensity was monitored at a wavelength of 610 nanometers (nm), shorter than the laser beam wavelength of 632.8 nm. The superiority of this method of temperature measurement compared to that based on transmission measurements becomes evident from the fact that over the temperature interval from about 300° K. (27° C.) to about 400° K. (127° C.) the transmission of the dye solution changes by less than two percent over the measured length, while the luminescence to transmitted light ratio changes by about an order of magnitude.

While the sensor in the above example is a liquid solution, solid sensors, preferably in the form of short fibers, can also be used in a practical device.

An important advantage of the vibronic materials of this invention with respect to their use as temperature sensors is that the value of $E_v$, which determines the optimum temperature range of operation, can be chosen and varied at will over a continuum of values by choosing, for any given material, the photon energy of the excitation light relative to the energy of the excited electronic energy level. Thus, a single sensor can be used for measuring temperatures over a wide range from cryogenic temperatures up to the highest temperatures which the sensor can withstand without deterioration. An additional advantage derives from the fact that there are many luminescent vibronic materials having absorption and luminescence spectra over a wide spectral region from the ultraviolet to the near infrared. One can choose, therefore, the wavelength region most suitable to one's needs. For instance, if it is required to transmit the optical signal over long distances by a fiber optic cable, one would choose wavelengths longer than 700 nm for both the excitation and the emission beams.

In a preferred embodiment, one measures the ratio R of the luminescence intensity I to the intensity of the illuminating light transmitted (non-absorbed) by the sensor. In a clear medium, the fraction of the intensity of the illuminating (excitation) light which is transmitted by the sensor is, of course, equal to $(1-\alpha_v)$. Since the luminescence intensity I is proportional to $\alpha_v$, it follows that R obeys the relation $$R = A\left[\frac{\alpha_v}{1-\alpha_v}\right]$$

which at low optical densities becomes $$R = A\left[\frac{\exp(-E_v/kT)}{1-\exp(-E_v/kT)}\right] \quad \text{B.5A}$$

where A is a constant.

In addition to the advantage of allowing ratiometric measurements using a single, narrow band excitation light source (for instance, an inexpensive laser diode) and a single photodetector, the direct measurement of a temperature-dependent intensity of absorbed light by luminescence means has the additional advantage, compared to the measurement of a temperature-dependent transmitted light intensity, that the temperature coefficient of the generated luminescence intensity I is, a low optical densities, orders of magnitude greater than the temperature coefficient of the transmitted light intensity, thus allowing more accurate measurements with simpler equipment. An example follows. Suppose that $\alpha$ is equal to 0.01 at 300K, and that the value of $(E_v/k)$ is 1500 deg$^{-1}$. From equation B5, the value of I increases by 1.67 percent per degree change near 300K. The intensity of the transmitted light, however, increases by only 0.017 percent, which is difficult to measure with simple equipment, compared to the relatively easy measurement of a 1.67 percent change.

In another example of a temperature measuring system according to this invention, the sensor is a crystal of emerald. This material, also operative in the 700 to 900 nm region, can be used over a wide temperature range from below ambient to over 800° K. In general, inorganic vibronic materials, of which emerald is an example, are preferred over organic materials for use at temperatures higher than about 400° K. The luminescent centers in emerald are $Cr^{3+}$ ions. Other inorganic crystals doped with Cr(III) or other transition metal ions like Ni(II), Co(II) or V(II) are also suitable for the practice of this invention.

Figure 8:
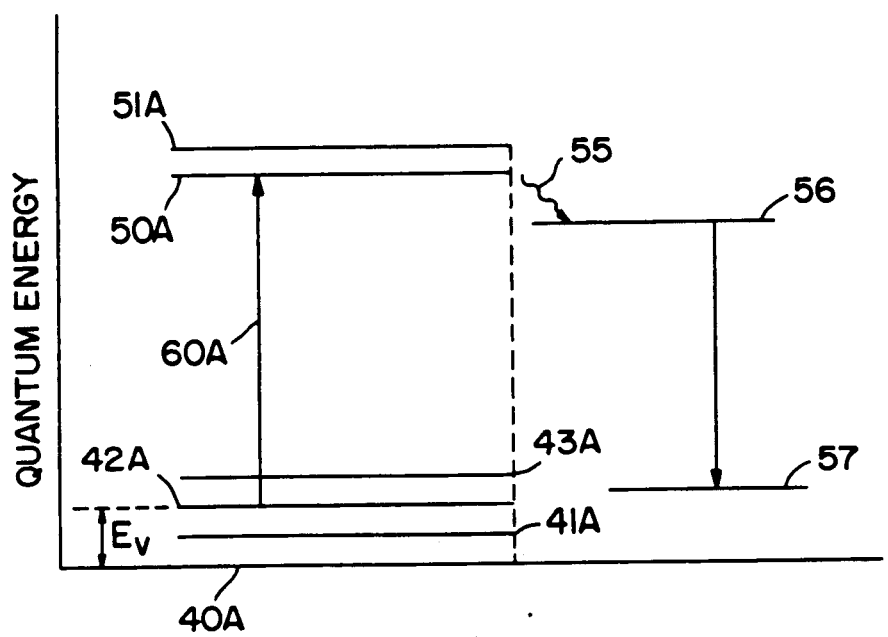
FIG. 8 shows the energy flow sheet, at the molecular level, of another luminescent material useful for measuring temperature according to the invention.

Another class of vibronic materials also suitable for use as temperature sensors are described with reference to FIG. 8, which shows an energy "flow sheet" at the molecular level. Excitation of molecules occupying a vibrational sublevel proceeds in the same manner as shown in FIG. 2 for the materials discussed hereinbefore. Levels 40A, 41A, 42A, 50A and 51A are similar to levels 40, 41, 42, 43, 50 and 51, respectively. The same digits in both figures indicates the similarity of the excitation processes, and the A's have been added to the levels of FIG. 4 to indicate that these levels belong to a different class of vibronic materials. The main difference is that in this class of vibronic materials the optically excited electronic level 50A transfers at least a major part of its absorbed energy, via a radiationless decay represented by the wavy line 55, to the lower level 56, of the same or a different molecular species. Luminescence emission occurs from level 56 to a lower level 57 or to any other lower-lying levels which may or may not include any of the levels 40A, 41A, 42A or 43A. Examples of this class of vibronic materials include virtually all phosphorescent organic dyes, luminescent chelates of Tb(III) and Eu(III), and some solid solutions of inorganic vibronic materials co-doped with other luminescent centers. Examples of the latter are crystalline or glassy materials co-doped with Cr(III) and Nd(III) ions, in which Cr(III) absorbs light and sensitizes the luminescence from Nd(III).

Two other classes of vibronic materials suitable for the practice of this invention are:

(a) luminescent lanthanide ions dissolved at high concentrations in crystalline or glassy hosts, and having at least one electronic energy level which can be thermally populated to a measurable extent at the temperatures being measured, and (b) luminescent semiconductors with a temperature-dependent absorption edge wavelength.

Both classes of materials are characterized by an absorption coefficient which, within a relatively narrow spectral region, increases exponentially with increasing temperature, in essentially the same manner as with the vibronic materials described hereinbefore. Therefore, they are used in the same manner and with the same methods which use vibronic materials.

In the preceding paragraphs I have described a method for measuring a physical parameter which produces a change in the optical density of the sensor. Since an optical density is also determined by the optical path length d, as expressed in equations B1 and B3, it follows that any physical parameter which changes the value of d can also be measured by this method. If the sensor is a liquid, as in the preceding example, the path length d can be varied by a mirror being displaced along the liquid in the direction of the interrogating light beam. Therefore, the same method can be used for measuring displacement or any other physical parameter, for instance pressure, which produces a displacement.

The use of luminescent materials for the conversion of a light attenuation having a low coefficient for the variable being measured into a luminescence signal having a high coefficient for the same variable can be applied to the measurement of any physical variable which can be made to produce an attenuation of the intensity of a probing light beam. For instance, a known method for measuring a physical variable with fiber optic systems involves subjecting a clad optical fiber to the action of the variable in such a manner that the fiber undergoes a deformation, said deformation resulting in the attenuation of the light intensity launched into the fiber core, with a corresponding increase in the intensity of the light which enters the cladding of the fiber. The conventional way of estimating the physical variable is to measure said light attenuation indirectly, by measuring the intensity of the light transmitted by the core. The method described above, whereby a temperature-dependent absorption is converted into a luminescence intensity, can be extended to the measurement of the light intensity forced into the cladding by the action of the physical variable being measured. Thus, the light intensity entering the cladding can be converted into a luminescence light intensity having a wavelength different from that of the probing light. Even if the attenuaoccurs from the ground state or from a vibronic level of the luminescent material. Therefore, a vibronic material having two emissive levels in thermal equilibrium provides at least two independent phenomena useful for measuring temperatures: (a) the temperature-dependent absorption process, discussed with reference to FIG. 5, and (b) the process discussed in this section.

Figure 10:
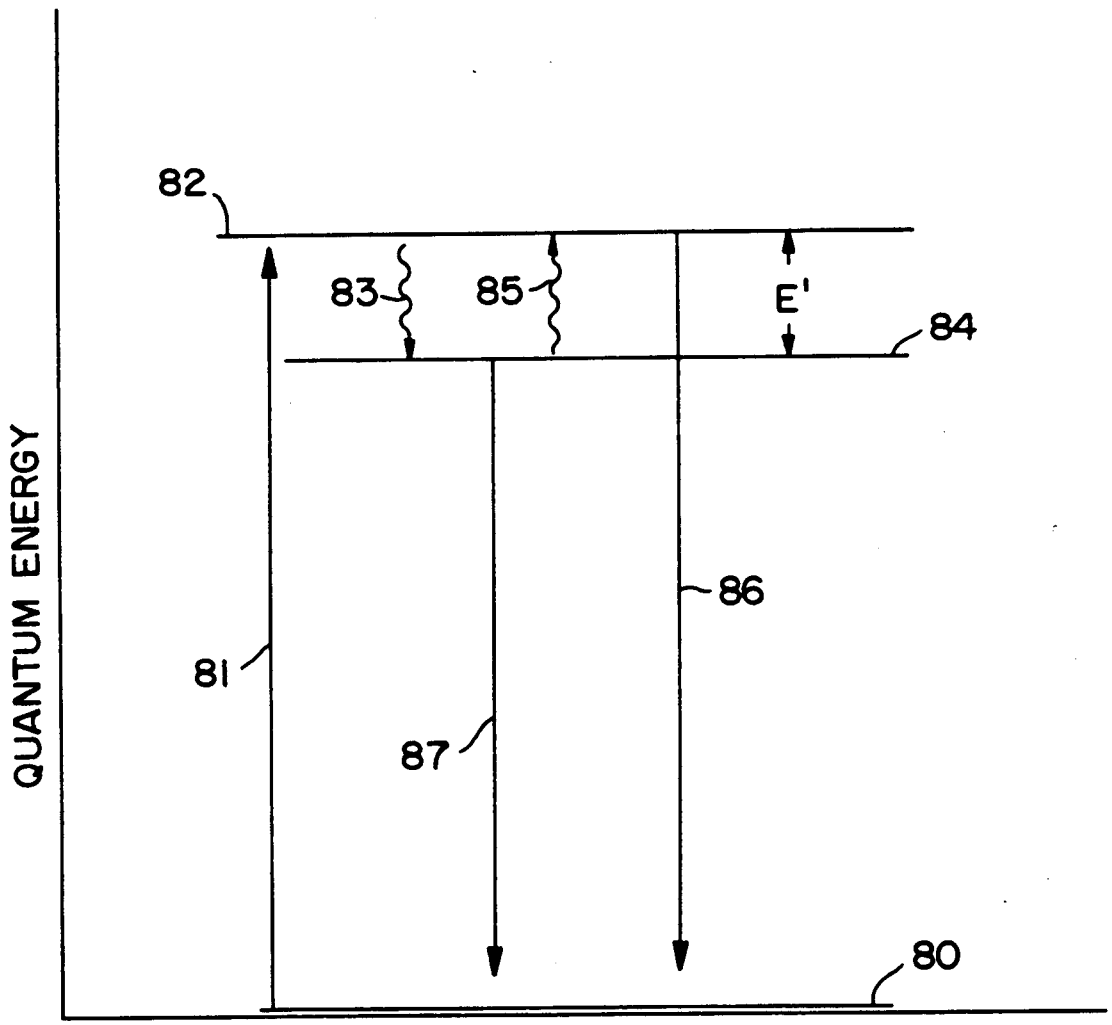
FIG. 10 shows an energy flow sheet at the molecular level of another kind of luminescent material useful for measuring temperature according to the invention.

The temperature range of operation of a thermometer based on the process described in FIG. 10 depends on the value of E'. A good signal-to-noise ratio is generally obtained when the value of E' is between about 3 kT and 10 kT. The method described herein is especially valuable for measuring cryogenic temperatures. When E' is of the order of 20 cm$^{-1}$ or less, temperatures in the liquid helium region are easily measured. Suitable sensors may be chosen from among a large number of materials with degenerate emissive levels with energy splittings E' within said range.

Self-Checking Features of the Disclosed Embodiments

A considerable amount of time is spent in industry checking the accuracy of thermometric devices. Checking procedures usually require the use of an auxiliary, calibrated thermometric device.

The method and materials disclosed herein permit automatic independent checks of the accuracy of measurements carried out according to any of the methods disclosed hereinbefore, without the need of any additional sensor, light source, photo-detector or optical component. For instance, many vibronic materials characterized by a temperature-dependent light absorption and fluorescence intensity, determined by the occupancy number of a vibronic level, are also characterized by a luminescence decay time and/or a spectral distribution of the luminescence, both of which are also temperature-dependent, but do not depend on the occupancy number of any vibronic level. Therefore one can, by simply adding inexpensive electronic processing components, compare a temperature reading operationally determined by the occupancy number of a vibronic level of the sensor to a temperature reading determined by the luminescence decay time or/and the luminescence spectral distribution of the same sensor, the measurements being all carried out simultaneously or sequentially by means known in the prior art.

The feature of this invention affording the capability of measuring, as temperature indicators, two independent physical parameters with a single probe, can be extended to the measurement of two *different* physical variables with the same probe. An example is the simultaneous measurement of displacement and temperature, as described hereinafter.

C. New Fiber Optic Sensors Based on Core/Cladding Light Coupling

Figure 11:
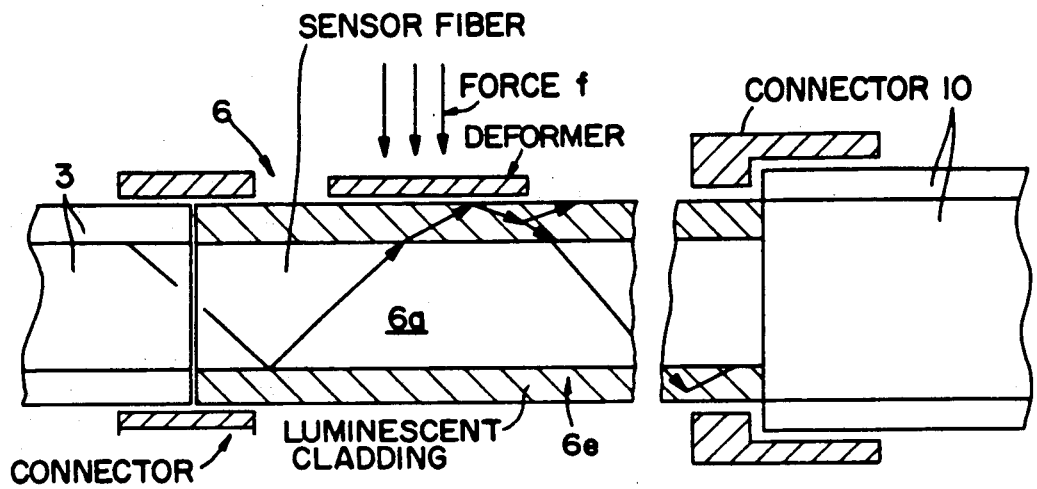
FIGS. 11 and 11' show a force sensor based on core/cladding light redistribution according to the techniques of this invention.
Figure 11:
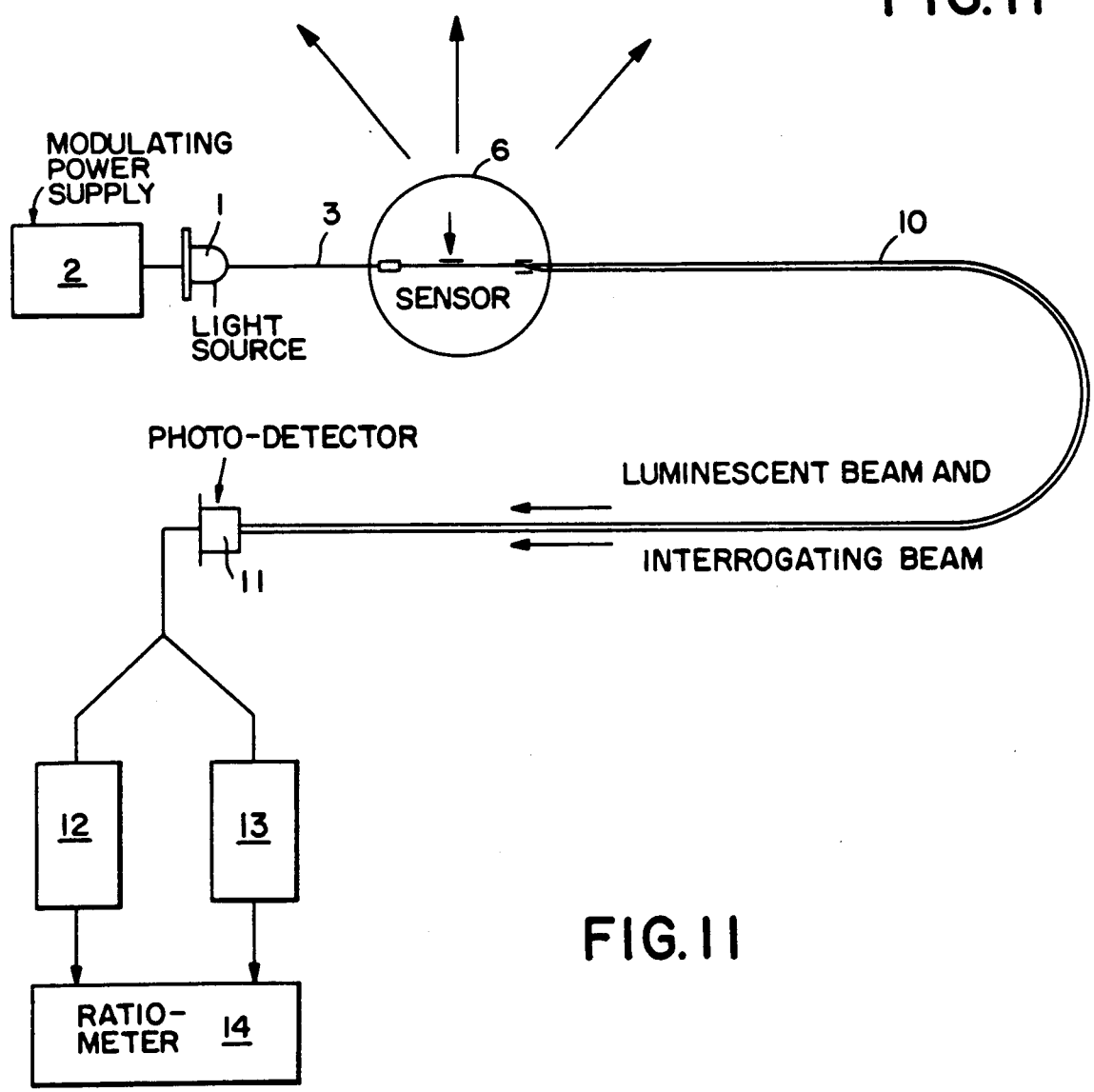

FIGS. 11 and 11' illustrates a new method, based on the present invention, for measuring the ratio of the intensity of the core modes to that of the cladding modes in fiber optic sensors based on core/cladding light coupling. The method uses as the sensor a fiber segment 6 having a low attenuation core and a cladding having dissolved therein a luminescent solute which will absorb the fraction of the intensity of the interrogating light beam in the core which is coupled to the cladding by the action of the variable being measured (this action is explained in detail in the following discussion). The method is carried out as follows:

A light source 1, which produces pulsed or AC-modulated light with a decay time of the order of 10$^{-5}$ seconds or shorter, driven by power suppy 2, launches an interrogating light beam into fiber 3. The end of this fiber is connected to the sensing fiber 6.

The measured variable, which may be temperature, pressure, weight, sound or the like, is represented by force f. Under the action of force f, a fraction of the intensity of the interrogating light beam travelling through core 6a is coupled to cladding 6e, where it generates luminescence light of a wavelength longer than that of the interrogating light. Both the attenuated interrogating light beam and the luminescence beam are fed to fiber 10 connected to the sensing fiber. Fiber 10 carries both beams to a measuring station where the two beams are separated, measured and ratioed by techniques known in the art, the intensity ratio of the two beams being an indicator of the value of the measured variable. The interrogating light beam and the luminescence beam can be separated in the time domain as well as in the wavelength domain, by any of the means described hereinbefore.

An example of a luminescent cladding which can be used in such a system is a styrenic elastomer containing a 16, 17-dialkoxyviolanthrone dye. The illuminating (interrogating) light beam can be produced by a gallium phosphide light emitting diode with a peak spectral output at about 660 nanometers (nm), which overlaps the peak absorption wavelength of the dye. The dye fluoresces in the 700 to 800 nm region.

A core/cladding light redistribution can occur not only under the action of a mechanical force, but also via a change in the refractive index of either the cladding or the core. One can, therefore, use the method described in connection with FIGS. 11 and 11' to measure refractive indices and/or any variable which changes the value of a refractive index including, but not limited to pressure, temperature, sound, concentration of solutes in liquid solutions, etc. Because this method allows the measurement of the cladding modes independently of the core modes, it is capable of very high sensitivity. This can be understood by analogy with the relative sensitivities of analytical techniques based on light transmission measurements compared to fluorometric measurements. At optical densities of the order of 10$^{-3}$ or lower, transmission measurements with an accuracy of, say, one percent, require the measurement of fractional changes of the order of 10$^{-5}$ or smaller. On the other hand, if the absorbing material is an efficient fluorescer, one could measure the same optical densities by measuring fluorescence. In this case, an accuracy of one percent on a measurement of an optical density of 10$^{-3}$ requires a signal change of only one percent.

The method described with reference to FIGS. 11 and 11' can be adapted to the well-known microbending technique disclosed by J. Fields and J. Cole, *Applied Optics* 19, 3265 (1980) which, as introduced by the authors, has the shortcomings common to techniques using attenuation measurements, described hereinbefore.

Figure 11A:
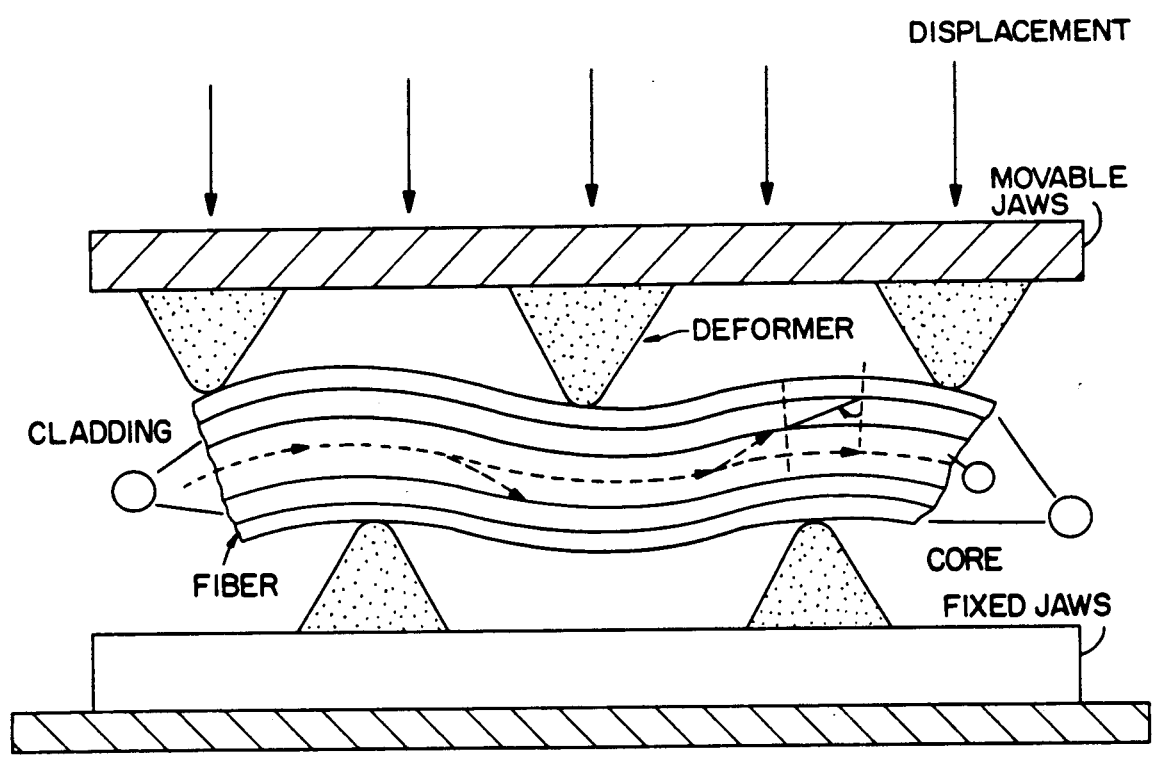
FIG. 11A illustrates a prior art fiberoptic microbender.

In a typical microbender, shown schematically in FIG. 11A, an optical fiber is placed against a set of stationary jaws or pins. An upper set of jaws or pins is connected to a movable element, the downward displacement of which introduces small bends in the fiber, causing a fraction of the intensity of the interrogating light propagating along the fiber core to be forced into the fiber cladding, the value of the fraction being detertion of the core light is too small to be measured accurately, the fluorescence from the cladding will have a much greater coefficient of change with respect to the measured variable.

Figure 9:
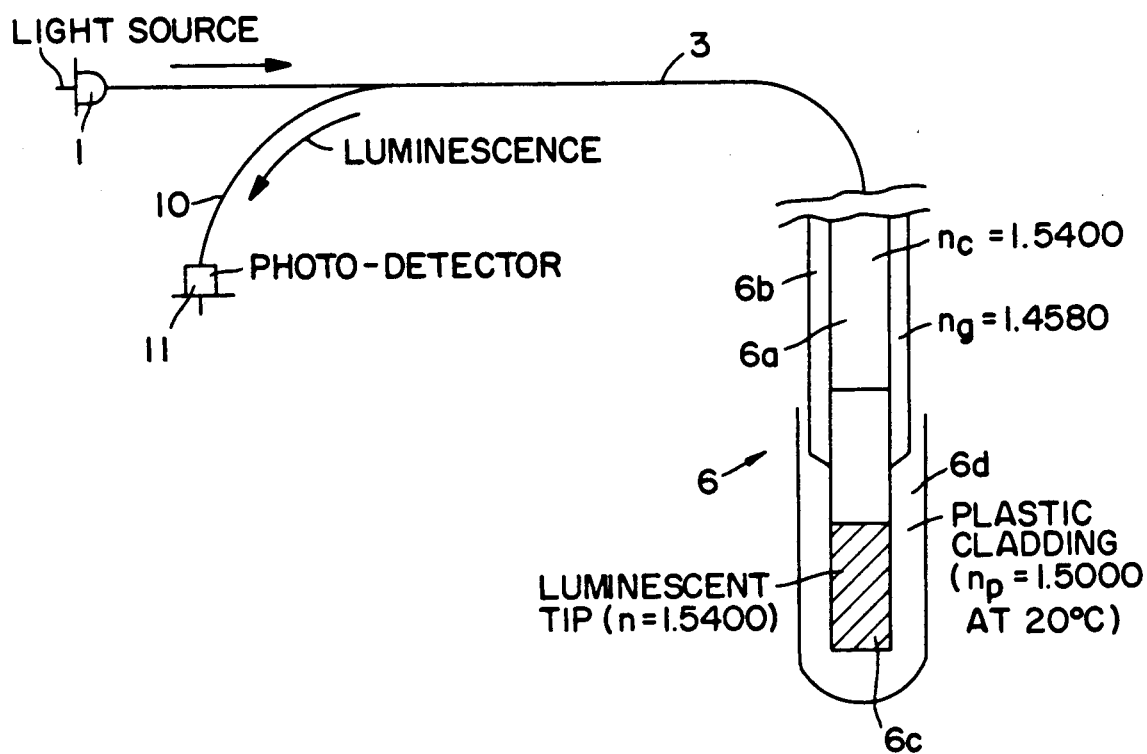
FIG. 9 shows a refractometric temperature sensor based on the invention.

Yet another method for measuring temperature with fiber optic systems is described as follows:

Some clear plastics like polyurethanes have a refractive index (RI) which varies appreciably with temperature. This property is the basis for the temperature measuring method described as follows:

Consider (FIG. 9) a glass-clad fiber, probe 6, with the tip of the core $6a$ terminated in a short length $6c$ of a luminescent material. Part of the glass cladding $6b$ is removed from the tip up to a short length above the luminescent segment, as shown in FIG. 9, and the temperature-sensitive polymer is applied instead as a new cladding $6d$.

In one example, the refractive indices of the core, glass cladding and plastic cladding are $n_c$ (core) = 1.5400
$n_g$ (glass cladding) = 1.4580
$n_p$ (plastic cladding) = 1.5000, at $T_o = 20°$ C.

The RI of the luminescent fiber core is assumed to be the same as that of the core of the glass-clad fiber, 1.5400.

As the interrogating light beam crosses the boundary between the glass-clad and the plastic-clad regions, its intensity I will be attenuated to the value given by the relation $$I = I_o[(NA)_p/(NA)_g]^2 \qquad B.6$$

where
$I_o$ is the intensity of the light beam before crossing the boundary;
$(NA)_p$ is the numerical aperture of the plastic-clad segment, and
$(NA)_g$ is the numerical aperture of the glass-clad fiber.

The intensity of the luminescence light generated in the luminescent tip and trapped therein by total internal reflection will be $$I_l = K \cdot I[(NA)_p/(NA)_g]^2 \qquad B7$$

where K is a constant determined mainly by the luminescence quantum efficiency of the luminescent material.

Equations B.6 and B.7 combine to give $$I_l = K' I_o \cdot (NA)_p^4 \qquad B8$$

where K' is the product $K \cdot (NA)_g^{-4}$

As the temperature changes from $T_o$ to $(T_o + \Delta T)$, $n_p$ will change from $n_{p,o}$ to $(n_{p,o} - \Delta n_p)$, and the value of $(NA)_p^4$ will change according to the relation $$(NA)_p^4 = (NA)^4_{p,o} \times [1 + A(\Delta n_p)]^2 \qquad B.9$$

where A is a constant.

For example, an increase of 1° C. will increase the value of $I_l$ by 3 percent when the temperature coefficient of the index of refraction is about $6 \times 10^{-4}$ RI units per degree Celsius.

Yet another method of this invention for the optical measurement of temperatures uses the properties of a class of materials characterized by having a Boltzmann equilibrium between the occupancy numbers of two excited emissive levels, contributions of which to the total luminescence intensity varies as known function of temperature. In contrast to the materials disclosed in U.S. Pat. Nos. 3,639,765; 4,061,578; 4,075,493; and 4,215,275, characterized by a decrease in the luminescence intensity of the higher of two emissive levels with increasing temperature, the luminescence from the higher level in the materials of this invention becomes more intense at higher temperatures. The processes responsible for this intensification are illustrated in FIG. 10, to which the following description applies. Molecules or ions of the luminescent material occupying the ground electronic level 80 are excited by absorption of light, as depicted by the arrowed line 81, to the emissive level 82, from which they decay rapidly, via the radiationless process 83, to the long-lived level 84. A fraction of the molecules or ions occupying level 84 are thermally excited, via radiationless step 85, to level 82, the occupancy number of which, relative to level 84, follows approximately the relation, in absence of level degeneracy, $$(N_{82})/(N_{84}) = \exp(-E'/kT) \qquad \ldots B10$$

wherein $N_{82}$ and $N_{84}$ are the occupancy numbers of levels 82 and 84, respectively, and E' is the energy difference between these levels. Levels 82 and 84 emit luminescence via radiative decays 86 and 87, with radiative rate constants $k_r$ and $k_r'$, respectively. The ratio R' of the luminescence intensity from level 82 to that of level 84 follows approximately the relation $$R' = k_r'(N_{82})/k_r(N_{84}) \qquad \ldots B11$$

or $$R' = (k_r'/k_r) \exp(-E'/kT) \qquad \ldots B12$$

Equation 8 shows that R' increases exponentially with increasing temperature. The value of R' is measured by ratioing the spectrally resolved luminescence intensities from both levels or, often more conveniently, by measuring the total decay time $\tau$ of the luminescence, which decreases with increasing temperature according to the relation $$\tau = [k_r + k_r' \exp(-E'/kT)]^{-1}[1 + \exp(-E'/kT)] \qquad \ldots B1$$

A measurement of $\tau$ gives, therefore, an indication of the sensor temperature. The preceding treatment is applicable when the excitation light generates luminescence from only one kind of emissive center in the sensor. If this condition is not met the luminescence response deviates somewhat from the predictions of the preceding equations. Said deviation does not affect the usefulness of this method of measuring temperatures. In practice the sensor is calibrated by obtaining a $\tau$ v temperature curve within the desired temperature range with the aid of a precision reference thermometer, and storing said information in an electronic memory. Measurements made afterwards with the luminescence sensor are compared automatically with the stored information by means of a microprocessor and/or other inexpensive electronic components, and the measured decay times are thus converted into reliable temperature readings. Examples of sensors useful with this method are crystals of $Al_2O_3$, beryl, MgO, and garnets, doped with Cr(III) or V(II).

The temperature variation of the decay time is independent of whether the excitation of the luminescence mined by the magnitude of the downward displacement of the movable element.

An alternate embodiment to the one described in FIGS. 11 and 11' is described with reference to FIGS. 12 and 12'. In this case the sensor fiber has a non-luminescent cladding 6b, and it is the core modes that are converted into a luminescence signal by means of a luminescent converter 8. Then both the cladding modes and the luminescence-shifted core modes are carried to the detection station as in the previous example. For good collection efficiency of the cladding modes, the cross-section area of the cladding should preferably be greater than that of the core. Even then, some of the cladding light enters the core and is converted into luminescence. For this reason this method is applicable mainly to the measurement of variables which couple only a small fraction of the intensity of the core light into the cladding, so that the cladding light contribution to the core-derived luminescence is minimal. In such case this alternate method has the advantage over the one using a luminescent cladding in that it produces a significantly stronger signal from the cladding modes.

D. Measurement of Index of Refraction of Fluids

Figure 13:
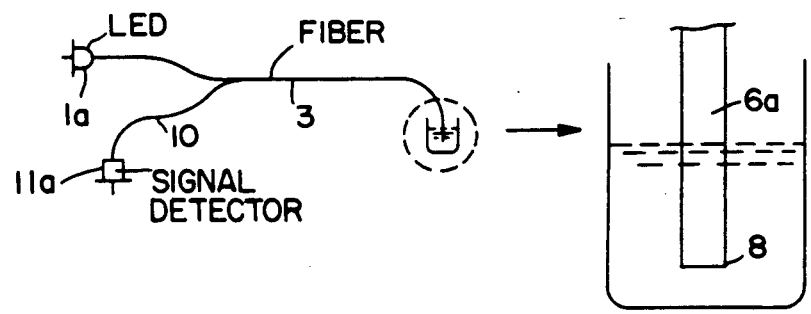
FIGS. 13 to 15 show different embodiments of refractometers according to this invention.

A fiber optic refractometer according to the teachings of the present invention is illustrated by FIG. 13. An unclad segment 6a of an optical fiber having a large numerical aperture (NA) is terminated in a luminescent tip 8. The fiber is optically connected to the illuminating light source 1A and a photodetector 11a. When the fiber fiber segment is immersed in the liquid to be measured to a point above the luminescent tip, the interrogating light beam entering the immersed length with an optical power $P_o$ is attenuated to a power $P_L$ given by the expression $$P_L = P_o[(NA)_L/(NA)_a]^2 \quad \text{D.1}$$

where $(NA)_L$ is the numerical aperture of the immersed unclad fiber segment and $(NA)_a$ is the numerical aperature of the fiber segment above the liquid. $(NA)_L$ obeys the relation $$(NA)_L = (n^2_c - n^2_L)^{0.5} \quad \text{D.2}$$

where $n_c$ is the refractive index of the fiber core material and $n_L$ is the refractive index of the liquid. The attenuated interrogating light beam excites the luminescence of the tip. The fraction $I_L$ of the luminescence intensity which is directed to the fiber segment above the liquid is given by the relation $$I_L = K \cdot P_L \cdot \alpha \cdot \phi \cdot (NA)_L^2 \quad \text{D.3}$$

where $\alpha$ is the fraction of $P_L$ which is absorbed by the luminescent material; $\phi$ is the luminescence quantum efficiency and K is a constant unrelated to $n_L$. Combining equations D.1, D.2 and D.3 the following equation results.

$$I_L = K' \cdot P_o (n^2_c - n^2_L)^2 \quad \text{D.4}$$

where $K' = K \cdot \alpha \cdot \phi \cdot (NA)_a^{-2}$. By dividing the value of $I_L$ by the intensity of the back-scattered interrogating light beam, the value of $n_L$ is obtained, unaffected or only minimally affected by fluctuations of the value of $P_o$, fiber or connector losses.

Any physical variable which affects the value of the refractive index of a material can be measured in a similar manner. An optical temperature probe based on refractive index changes is described in another section of this disclosure.

Other Embodiments of Refractometers with Fiber Optic Links

Fiber optic refractometers based on the principle of light attenuation due to a decrease in the numerical aperture of a liquid-clad fiber are capable of high sensitivity. Their accuracy is limited, however, by any build-up of contaminant films at the fiber probe. Refractometers based on angular deflection of the interrogating light beam are less affected by contaminant films, as the angle of deflection is essentially independent of any light attenuation due to said films.

Figure 14:
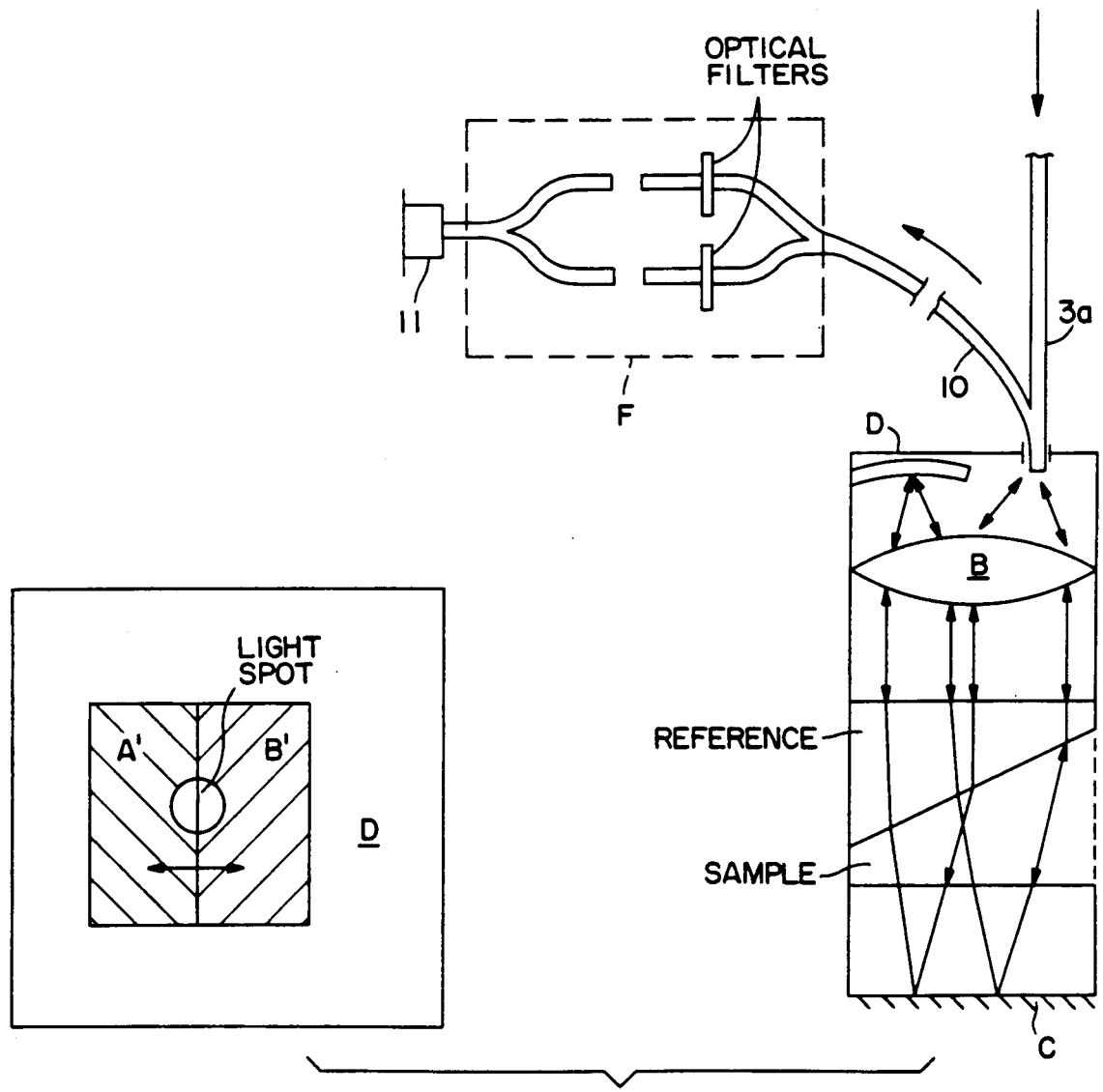

One problem that must be solved before a remote, passive deflection refractometer can be realized is how to convert the deflection of a light beam into an optical parameter which is unaffected by fluctuations of the intensity of the interrogating light beam, fiber and/or connector losses or detector drift. This invention includes a device in which this problem is solved. The device is illustrated in FIG. 14.

An interrogating light beam exiting from the common tip of the bifurcated fiber 3a is collimated by lens B and passes through both the reference material and the liquid sample to be measured, before being reflected by mirror C. The reflected beam passes again through both the sample and the reference material, and is focused by lens B into a luminescent screen D coated with a variable optical density metal film. The position of the focused spot is a function of the refractive index of the liquid sample, and the optical density of the metal film is a known function of the position of the focused spot. The focused spot will then produce a luminescent beam and a reflected beam, the intensity ratio of which is a unique function of the refractive index of the liquid being measured, independent of the intensity of the interrogating light beam. The luminescent and reflected beams are sent back to the fiber 3a and to the photodetector 11. The photodetector receives each beam alternately through an optical filtering and switching assembly F. Since both beams travel through the same fiber, any optical losses are cancelled by ratioing the signals (assuming that their wavelengths are sufficiently close to neglect dispersion effects). The ratio so obtained is, then, a unique function of the refractive index of the liquid, unaffected (or only minimally affected) by fluctuations of the intensity of the interrogating light beam, fiber and/or connector losses or detector drift.

The description of the preceding paragraph can be used to design other variations of a refractometer. For example, one can measure very small displacements of the focused light spot by focusing it on a screen sharply split into a reflective half and a luminescent half as shown in the box insert to FIG. 14, or into two luminescent halves each emitting luminescence in different wavelength regions. With a light spot of, say, 10 micrometers diameter, one can measure displacements of the order of 10 nanometers or smaller corresponding to refractive index changes of the order of $10^{-7}$ RI units or less.

Another embodiment of a refractometer according to this invention, particularly useful for measuring the refractive index of turbid liquids, is described with reference to FIG. 15.

Figure 15:
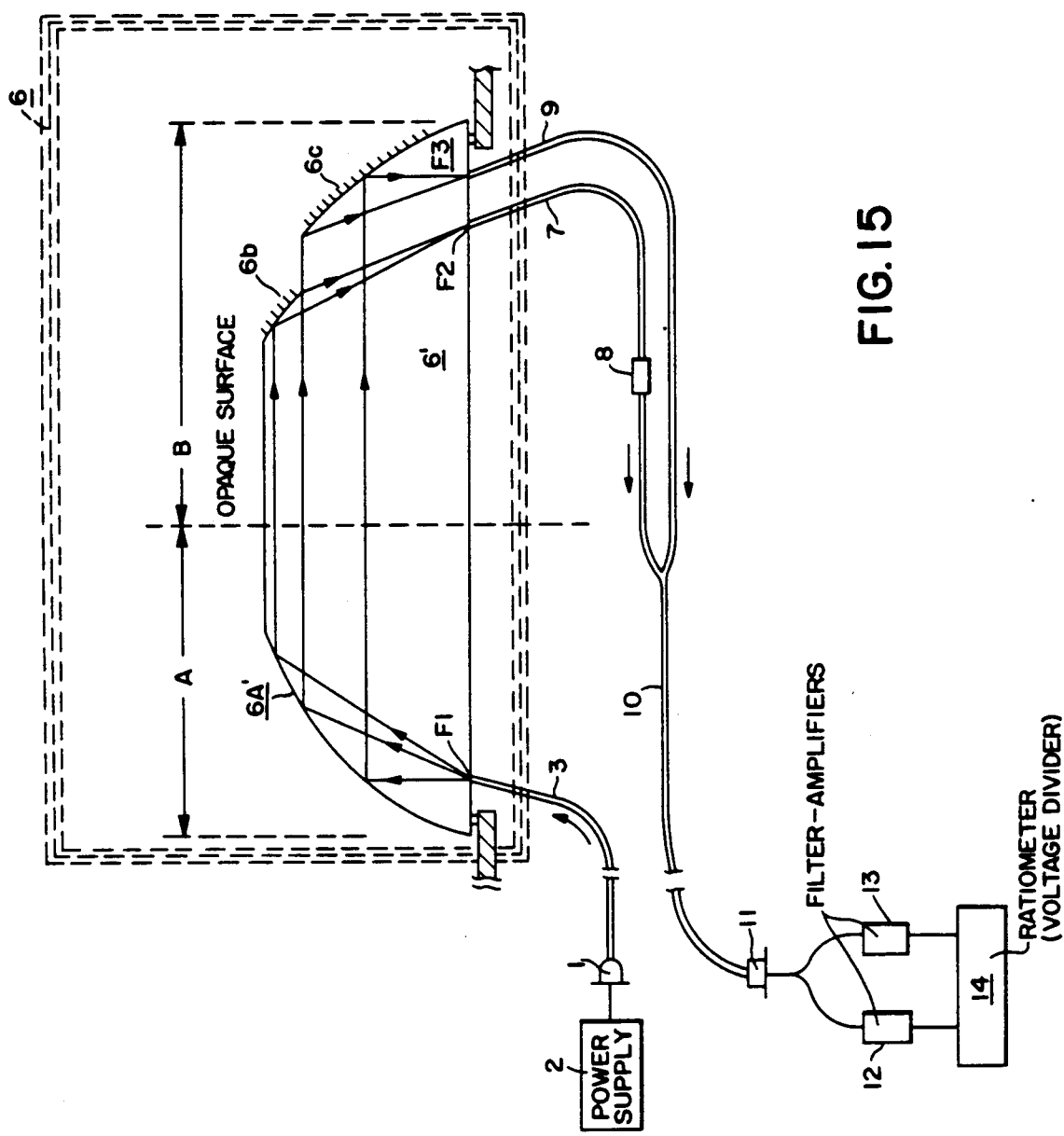

Referring to FIG. 15, the probe is a clear solid 6' having, in part, a parabolloidal section 4A with a smooth, polished surface. The tip of an optical fiber 3 is placed at focal point F1 of the parabolloidal section, while the other tip receives light from light source 1. The light input into the fiber consists of a train of regularly recurring pulses with a decay time $\tau_1$ of about $10^{-6}$ seconds or shorter, as described hereinbefore in Section A entitled "A General Ratio Method for Measuring Physical Variables with Fiber Optic Systems." The probe 6' has two regions A and B. Region A comprises the parabolloidal surface at which the light rays emerging from fiber 3 are reflected in a direction parallel to the optical axis of the solid, defined as the line passing through points F1, F2 and F3. Region B is so shaped that said reflected rays are focused, through a second reflection, at points F2 or F3, depending on whether their angles with the normal to the parabolloidal surface of the solid are larger or smaller than the critical angle $\theta_c$ for total internal reflection (TIR). The tips of optical fibers 7 and 9 are located at points F2 and F3, respectively.

When the probe is in contact with the liquid being measured, the intensity ratio of the light beams focused on points F2 and F3 is a function of the critical angle $\theta_c$, and this is determined by the relation:

$$\sin\theta_c = n_L/n_s$$

where $n_L$ is the refractive index of the liquid being measured, and $n_s$ is the refractive index of the probe material.

The light beam carried by fiber 7 is converted by luminescence converter 8 into a luminescence light with a decay time $\tau_2$ much longer than $\tau_1$. Both the luminescence light and the light carried by fiber 9 are joined into fiber 10 and carried to photodetector 11, where their relative intensities are measured as described hereinbefore. The ratio of their intensities is an indicator of the refractive index of the liquid.

A similar approach can be used with probes using flat solid/liquid interfaces, which are commonly used in refractometers using the principle of Frustrated Total Internal Reflection (FTIR).

E. The Measurement of Liquid Level

One unique and very useful characteristic of luminescent materials is that they introduce light propagation modes in the direction opposite to that of the interrogating light beam in fiber optic systems. Since the counter-propagating light is of a difference wavelength from that of the interrogating light beam, it can be readily measured even in the presence of large intensities of light backscattered from the interrogating light beam. This characteristic permits the construction of a simple liquid level meter.

Known liquid level meters based on refractive index changes at a fiber/fluid interface are "on/off" sensors which can tell only whether the fiber is immersed in the liquid, but cannot measure the actual liquid level above the lowest immersed point. The liquid level meter disclosed herein, also based on refractive index changes, uses a single fiber to determine the actual liquid level, and can measure continuous level changes as well.

Figure 16:
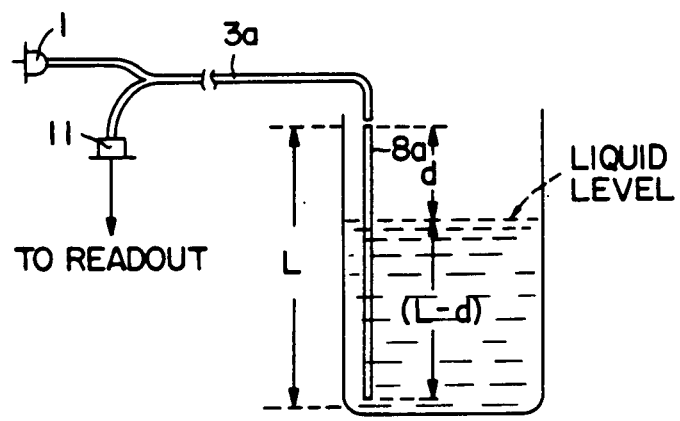
FIG. 16 is a schematic representation of an optical liquid level meter used according to this invention.

The level sensor of this invention is a luminescent optical fiber with a length no shorter than the highest level to be measured, and is so designed that the luminescence excitation radiation entering the dry fiber can be propagated to the other end, with a total attenuation by absorption preferably not greater than about 10 dB. Thus, every point along the fiber becomes a light source. The fiber is positioned vertically in the liquid container, which can be filled up to a maximum level of L meters from the bottom. The luminescent length of the fiber is, preferably, also equal to L. Inside the liquid vessel, the fiber has a non-immersed length d and an immersed length equal to (L−d). A practical arrangement for measuring the liquid level is illustrated in the accompanying FIG. 16. An excitation light beam from light source 1 is launched into one arm of the bifurcated optical fiber 3a, said fiber leading to and optically connected to the luminescent fiber 8a. The other arm of the bifurcated fiber directs a known fraction of the luminescence light returned to fiber 3a to photo-detector 11. The luminescence light intensity $I_L$ received by the photo-detector is determined by the liquid level according to the approximate relation:

$$I_L = K \cdot P_o \{\alpha_d + (1-\alpha_d)\alpha_L[(NA)_L/(NA)_d]^4\} \text{ photons} \cdot \text{sec}^{-1} \qquad \text{E1}$$

where

K is a constant determined by the luminescence quantum efficiency of the fiber and other level-independent factors;

$P_o$ is the excitation light intensity launched into the fiber within the fiber acceptance angle;

$\alpha_d$ is the fraction of $P_o$ absorbed by the non-immersed fiber segment;

$\alpha_L$ is the fraction of the light transmitted by the non-immersed fiber segment which is absorbed by the luminescent centers of the immersed segment;

$(NA)_d$ is the numerical aperture of the non-immersed fiber segment; and $(NA)_L$ is the numerical aperture of the immersed fiber segment.

The fourth power of the last term arises from the fact that the luminescence intensity transmitted by the immersed fiber segment to the detector is determined by the product of the efficiencies of two consecutive steps, namely (a) the collection of the excitation light beam by the immersed fiber segment, and (b) the collection and transmission of the generated luminescence by the immersed fiber segment.

The efficiencies of each of the steps (a) and (b) are directly proportional to the square of the numerical aperture of the immersed fiber segment.

Equation E.1 can be expressed more explicitly as $$I_L = K \cdot P_o\{[1-\exp(-\beta d)] + [\exp(-\beta d)][1-\exp(-\beta[L-d])][(n^2_c - n^2_L)/(n^2_c - 1)]^2 \qquad \text{E2}$$

where $n_c$ is the refractive index of the fiber material, $n_L$ is the refractive index of the liquid, and $\beta$ is the Naperian absorption coefficient of the fiber per unit length.

Figure 17:
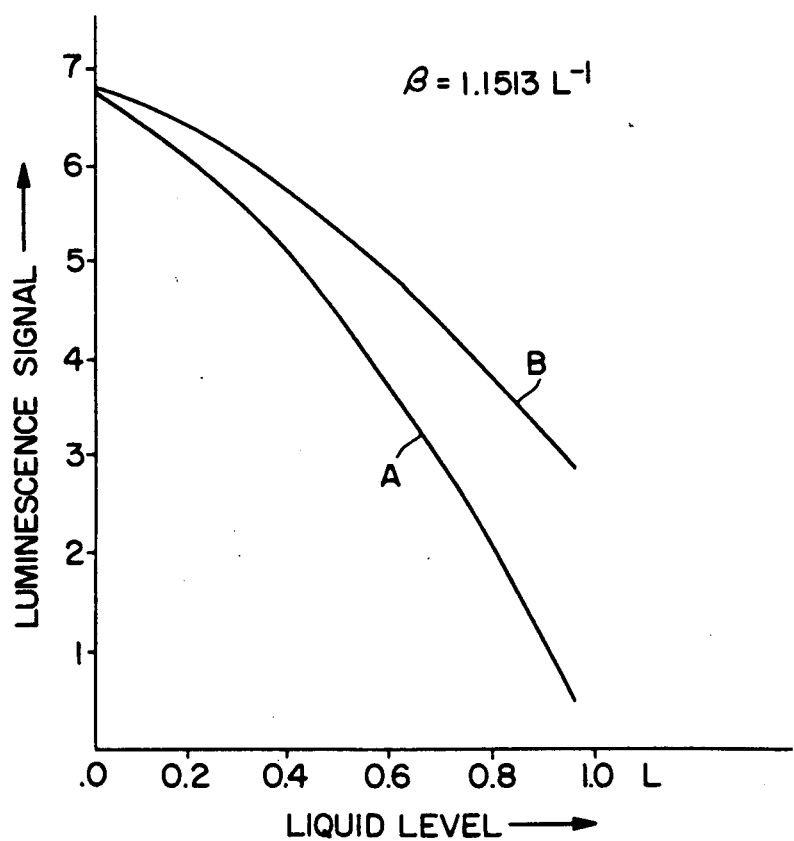
FIG. 17 shows luminescence intensity as a function of liquid level for a fiber optic liquid level gauge according to this invention.

The attached FIG. 17 shows the expected relative luminescence signals when a luminescent fiber is immersed in a tank where the maximum liquid level is equal to L, and $\beta$ is equal to 1.1513 $L^{-1}$. The fiber material is silica doped with a very small amount of the luminescent material (for instance $Nd_2O_3$), and its refractive index is 1.46. Two cases, A and B, are considered. In Case A, the refractive index of the liquid is only slightly smaller, equal to or greater than 1.46. In Case B, $n_L$ is 1.205, the index of liquid nitrogen. The fiber was assumed clean. (Fibers are expected to remain clean for a long time in liquids which dissolve grease, like petroleum liquids.)

The problem of fiber contamination should not arise in a potentially important application of this method, namely, the remote measurement of a variety of physical variables with transducers which use liquid column indicators.

F. A Fiber Optic Chemical Analyzer

It is known that virtually all chemical reactions release or absorb heat. Most chemical reactions used in analytical chemistry are exothermic, and the total amount of heat generated can be correlated with the amount of the analyte. It is possible to measure small temperature changes with fiber optic techniques, so one could develop in principle a universal fiber optic chemical analyzer. In order for the analysis to be specific for one single chemical species among many present in a mixture, one needs, of course, a highly specific reagent or catalyst. Enzymes are highly specific catalysts for a variety of analytes, and they can be immobilized on polymeric matrices.

Figure 18:
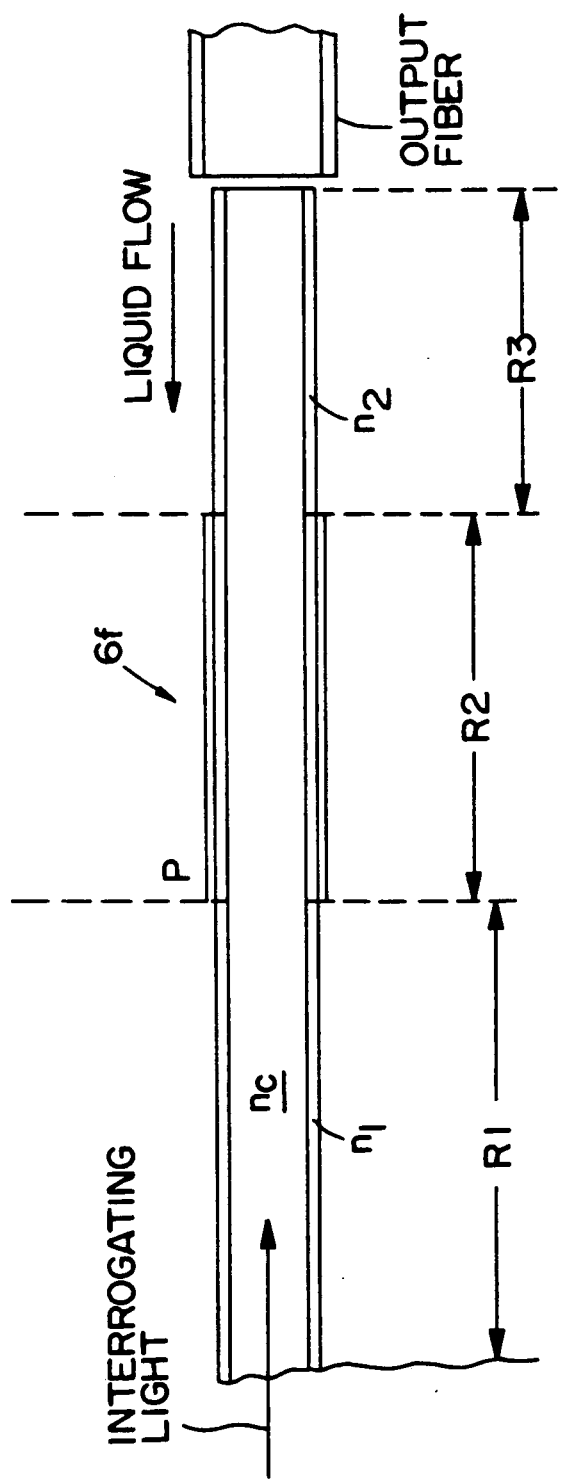
FIG. 18 shows a thermometric chemical analyzer based on core/cladding light coupling according to this invention.

The analyzer of this disclosure is described with reference to FIG. 18. It consists of a suitably modified optical fiber 6f comprising a core having an index of refraction $n_c$ and a cladding with an index of refraction $n_1$. The fiber has this cladding removed from a segment extending from point P to the right, and this segment is re-clad with a polymer having an index of refraction $n_2$ higher than $n_1$ but lower than $n_c$. This polymer is chosen from the class of polymers the indices of refraction of which have a relatively large temperature coefficient. The cladding contains dissolved therein a fluorescent dye which can be excited with light wavelengths present in the interrogating light beam lauched into the fiber by a light source. Region R2 of the new cladding is coated with a thin black layer, the purpose of which is to remove the light entering the cladding in this region. A thin polymeric layer having attached to it an immobilized enzyme specific to the analyte is coated on top of the black layer.

The analyzer works as follows: The liquid containing the analyte flows in the direction of the arrows over the new cladding. At the initial temperature $T_o$ a light beam launched into the fiber travels through the fiber core in Region R1 with an intensity $I_o$. Immediately after passing into region R2 the light intensity drops to the value $I_1$, given by $$I_1 = I_0[(NA)_2/(NA)_1]^2 \qquad F.1$$

where $(NA)_1$ and $(NA)_2$ are the numerical apertures of the fiber in regions R1 and R2, respectively. Equation (1) can also be written as $$I_1 = I_0[(n^2_c - n^2_2)/(n^2_c - n^2_1)] \qquad F.2$$

When an exothermic reaction occurs at the site of the immobilized enzyme, the refractive index decreases from $n_2$ to the value $(n_2 - \Delta n)$, and the intensity of the light beam entering the fiber core in region R2 increases approximately by an amount $$\Delta I = [(2n_2 \cdot \Delta n)/(n^2_c - n^2_1)] \qquad F.3$$

As the light beam reaches region R3 the increase $\Delta I$ is "lost" to the cladding, where it generates a luminescence intensity proportional to $\Delta I$ which is a function of $\Delta n$ and hence of the temperature rise of the cladding in region R2. This temperature rise is a specific indicator of the concentration of the analyte. Both the luminescence light and the interrogating light propagating through the fiber core are collected by an output fiber and directed to a photodetection station.

G. Optical Displacement And Position Transducers

It it well know that virtually all physical variables can be converted into a measureable linear or angular displacement. Thus, the pressure exerted by a mass of matter produces a downward displacement of a balance pan; temperature can be read from a linear displacement of a mercury column in a clinical thermometer; an electrical current produces an angular displacement of a needle indicator on the dial of an analog ammeter. Many household devices do in fact depend on the displacement of an indicator to inform the user of the magnitude of the physical variable being measured.

In most engineering fields, a linear or angular displacement is one of the most common means of measuring a physical variable. These measurements can be carried out remotely over optical fibers, but are subject to error due to fluctuations of the intensity of the interrogating light beam, fibers and/or connector losses or detector drift.

The use of luminescent materials according to the teachings of this disclosure permits the ratiometric measurements of said displacements, said measurements being unaffected or only minimally affected by the above sources of error. An example of a practical device for carrying out these ratiometric measurements according to the teachings of this disclosure is the absolute optical encoder described below with reference to FIG. 19.

Figure 19:
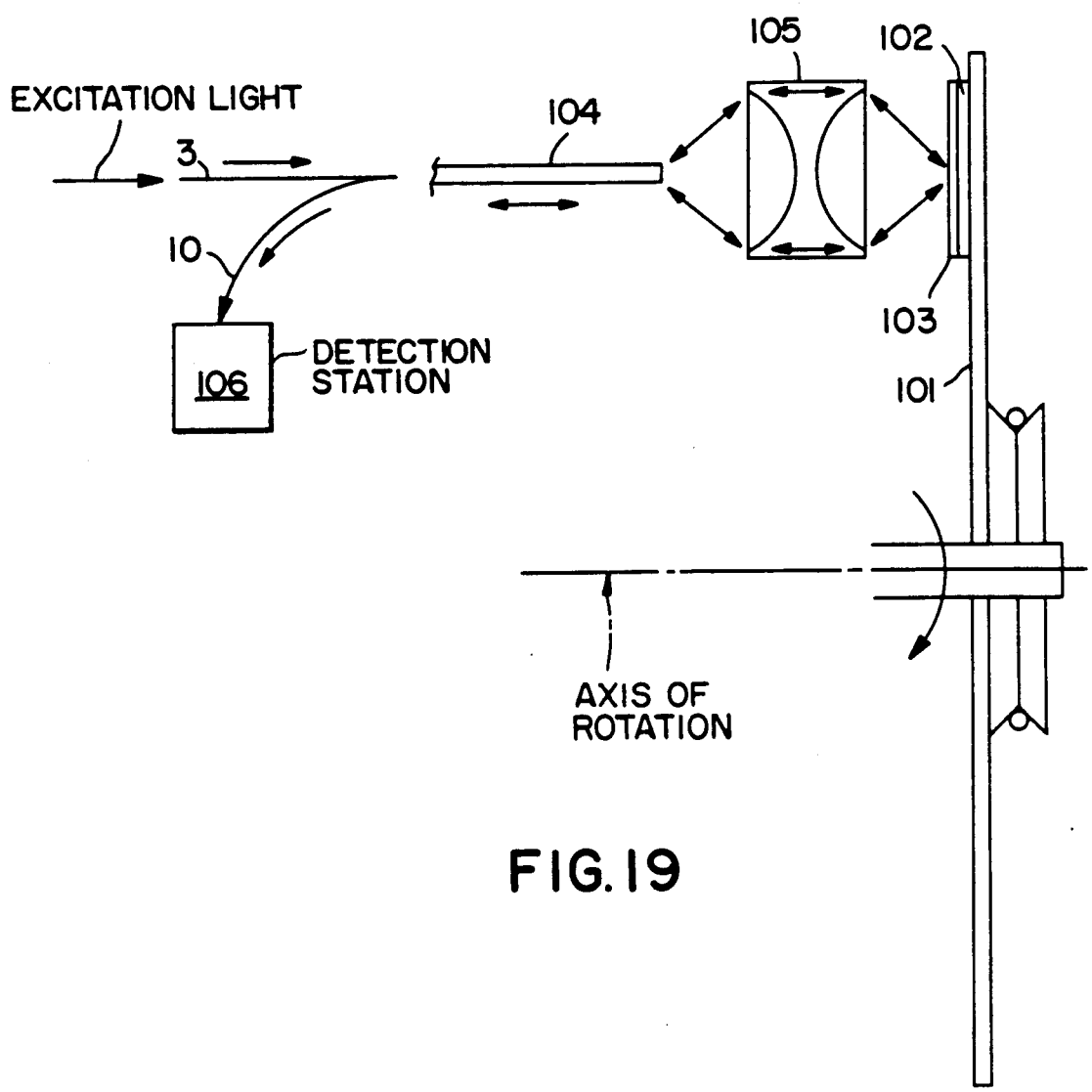
FIG. 19 shows an optical probe for measuring angular displacement according to this invention.

Referring to FIG. 19, a disk 101, the angular position of which is related in a known manner to the physical variable being measured, is coated with a uniform layer 102 of a fluorescent film. Layer 102 is covered with a metallic film 103 characterized by an optical density which varies as a function of angular position. The angular position of the disk is read with a fiber 104 having its tip optically connected to a lens 5, said lens focusing the interrogating light beam into a spot on the disk. At any spot in the disk, the reflectivity R and the transmissivity T of the metallic film are related by the equation $$R + T = K \qquad G.1$$

where K is a constant with a value near unity. The interrogating light beam focused at any spot in the disk produces both a reflected and a luminescent light intensity which are collected by the fiber/lens combination and sent to detection station 106 via fiber segment 10. The intensity ratio R' of the luminescence light to the reflected light reaching the detection station is given by $$R' + AT^2/(K-T) \qquad G.2$$

where A is a constant.

R' is a unique function of the angular position, unaffected or only minimally affected by fluctuations of the intensity of the interrogating light source or by losses in the fiber optic link. The effects of detector drift are eliminated by measuring both the reflected light and the luminescence light with the same detector.

A simple variation of the method described in the preceding paragraphs uses a light spot to illuminate a screen attached to the object undergoing a displacement. The screen includes two contiguous areas, a reflective one and a luminescent one, both on the surface of the screen instead of in the layered structure described above, and both illuminated simultaneously by the light spot. As before, the intensity ratio of reflected-to-luminescence light is an indicator of the screen position.

H. A Device for the Simultaneous Measurement of Temperature and Another Physical Variable With a Single Probe The creation of new light wavelengths and/or time domain frequencies according to the luminescence conversion methods of this invention makes it possible to construct simple sensors capable of measuring two different physical variables simultaneously using a single probe. A particularly useful application is the simultaneous measurement of temperature and any other physical variable which produces a change of light intensity.

Very often it is needed to measure both temperature and pressure. In the following paragraphs a method to measure both physical variables with a single probe is described.

Figure 12:
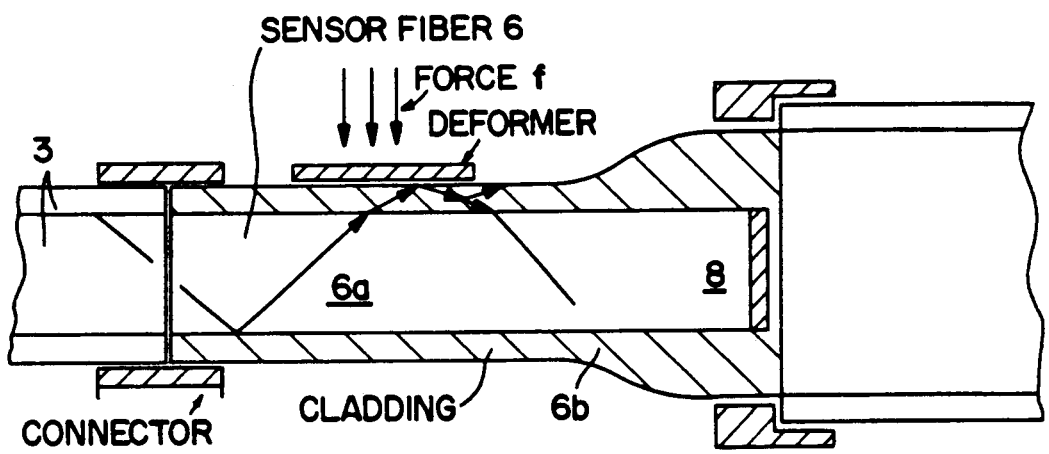
FIGS. 12 and 12' shows an alternate embodiment of a force sensor, also based on core/cladding light redistribution.
Figure 12:
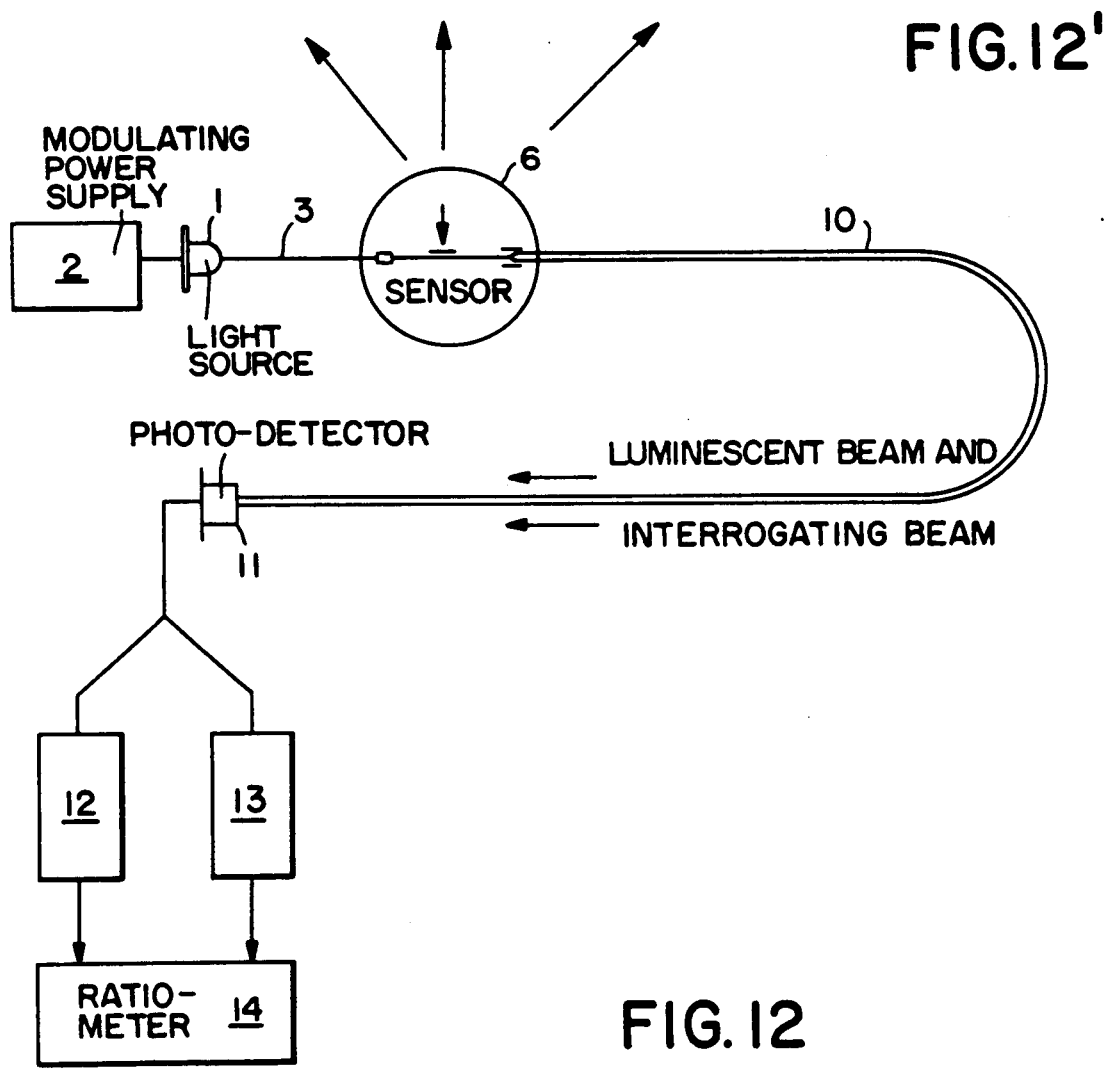

One preferred embodiment of an optical probe for measuring both temperature and pressure comprises an optical fiber consisting of a glass core and a cladding with a refractive index lower than that of the core, within an apparatus as shown schematically in FIG. 12. The deformer consists of a microbender attached to a pressure-sensing diaphragm by a stiff rod. The luminescent converter 9 is chosen from the class of materials with an essentially invariant luminescence quantum efficiency within the working temperature range, but with a luminescence decay time which varies appreciably as a function of temperature within said temperature range.

In operation, the sensor is interrogated with light pulses much shorter than the luminescence decay time $\tau$ of the converter, or with AC-modulated light with a period of oscillation much shorter than $\tau$.

Under the action of the measured pressure, the microbender "squeezes" light from the core to the cladding of the fiber. The intensity of this cladding light, divided by the intensity of the luminescence from converter, is an accurate indicator of pressure, while the measured luminescence decay time from converter is an accurate indicator of temperature.

Figure 20:
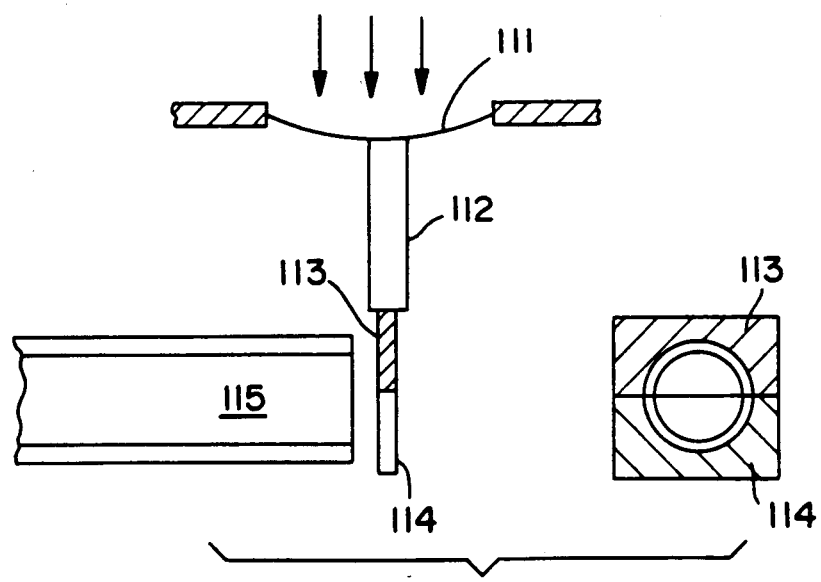
FIG. 20 shows a probe for the simultaneous measurement of displacement and temperature.

In another preferred embodiment, illustrated in FIG. 20, the pressure being measured deflects a diaphragm 111 to which is attached a push rod 112. Attached to the push rod is a screen split into a reflecting area 113 and a luminescent area 114. Opposite the split screen is a fixed optical fiber tip 115 which illuminates both areas of the split screen with light within a wavelength region $\lambda_o$. As the screen moves according to the deflection of the diaphragm, the relative intensities of the light reflected back to the fiber and the luminescence light of wavelength $\lambda_1$ (different from $\lambda_o$) emitted into the fiber change as a known function of pressure. It is not necessary to have a fixed light spot and a moving screen. One can, of course, attach the fiber tip to the push rod, and thus illuminate a stationary screen with a moving light spot.

In a variation of the above embodiment, both areas of the screen are luminescent. Referring to FIG. 20, if screen area 114 emits luminescence in a wavelength region designated here as $\lambda_1$, area 3 can be coated with another luminescent material which emits luminescence light within a wavelength region $\lambda_2$, which includes wavelengths not present in wavelength region $\lambda_1$, both regions $\lambda_1$ and $\lambda_2$ including wavelengths not present in the region $\lambda_o$ of the illuminating light.

The following analysis applies whether one or both screen areas are luminescent.

For small displacements of the center of the diaphragm, the displacement of the screen is a linear function of pressure. One can obtain a measurable ratiometric function of pressure as follows: Let A be the height of area 3 and B be the height of area 4 at a chosen reference pressure (for instance atmospheric pressure). An increase in pressure produces a downward displacement x of the screen, which will increase the optical signal from area 3 and decrease the optical signal from area 4, the ratio of the new signals being $$R = (A+x)/(B-x)$$

R is not linear with x, but one can obtain the function R' defined as $$R' = [(A+x) - (B-x)] / [(A+x) + (B-x)]$$

R' varies linearly with displacement, and is essentially unaffected by fluctuations in the intensity of the interrogating light source, fiber and/or connector losses or detector drift.

One example of a material constituting the luminescent area of the split screen is alexandrite, a chromium-doped crystal characterized by a luminescence quantum efficiency which is essentially invariant with temperature within the working temperature range, but with a luminescence decay time which is a measurable function of temperature within said range. (J. C. Walling et al. *IEEE J. Quant. Electron.* Q.E.-16(1982) p. 1302.) A measurement of the decay time of the luminescence thus gives an accurate indication of temperature. One can, thus, measure both pressure and temperature with a single probe.

Other chromium-doped crystals are also suitable for this purpose.

The above description shows that according to the teachings of this invention, any displacement or any other physical variable can be measured simultaneously with temperature. This has important applications, insofar as the response of transducers for most physical variables is affected by temperature to varying degrees. The simultaneous measurement of temperature allows the instrument designer to introduce an automatic temperature correction factor when any other physical variable is measured.

As pressure transducers one may use, besides diaphragms, capsules, bellows, Bourdon tubes and the like.

I. A Long, Continuous Optical Fiber Sensitive to Perturbations Along Its Whole Length A long optical fiber sensitive to perturbations along its whole length offers attractive potential applications in a variety of fields. It can function, for instance, as a tamper or intrusion indicator in security systems. Another potential application is in the area of industrial control systems, where one could attach a plurality of transducers at any points along the fiber without the need of cutting it. An internal telecommunications line in a building (office, factory, hospital, etc.) is another important potential application. A potential mass market exists in the construction and transportation industries, where the fiber could detect cracks and/or strain at a plurality of points in buildings, bridges, airplanes, ships, etc. This disclosure describes an embodiment of such a sensor, and its mode of operation.

Figure 21:
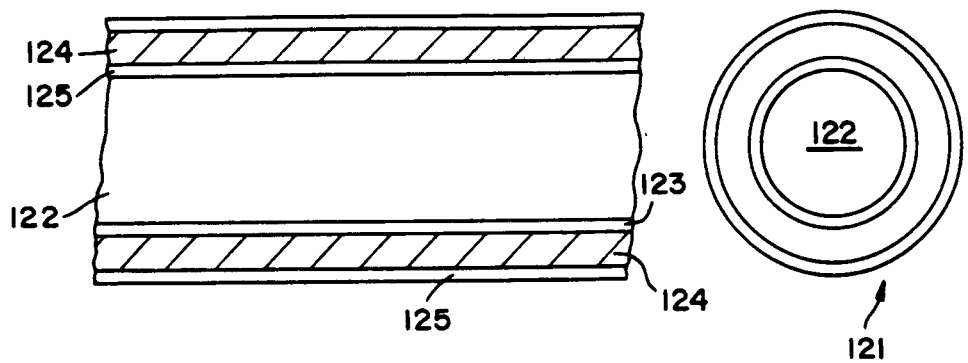
FIGS. 21 and 21' shows a long, continuous optical fiber sensitive to perturbation.
Figure 21:
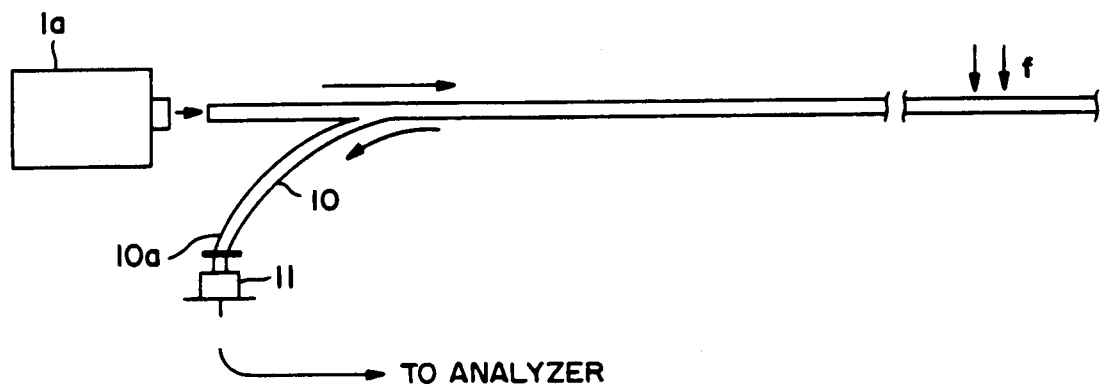

The sensor is described with reference to the accompanying FIGS. 21 and 21'. It consists of a fiber 121 with a glass core 122 having a refractive index $n_c$; a cladding 123 around the core, a few micrometers thick, made of a photoelastic material having an index of refraction $n_p$ lower than $n_c$; a plastic cladding 124 around cladding 123, having dissolved therein a fluorescent dye, and having a refractive index higher than $n_p$; and an outer cladding 125 around cladding 124, with a refractive index equal to or smaller than $n_p$. The sensor operates as follows:

A train of light pulses from a laser 1a, having a duration $\tau_o$ of the order of nanoseconds and a repetition rate greater than 100 pulses per second, is launched into the fiber. At any location where a force f is applied to the fiber, a fraction of the intensity of the light travelling through the fiber core "leaks" into cladding 124, where it generates fluorescence light pulses from the dye dissolved therein. A fraction of the intensity of the fluorescence light pulses is collected by fiber 121 and sent via fiber segment 10 to photodetector 11. Each fluorescence light pulse arrives at the photodetector at a time t from the start of the interrogating light pulse, determined by the relation $$t = 2d \cdot n_c \cdot c^{-1} \text{ seconds} \qquad \text{I.1}$$

where d is the distance between the sensor and the photodetector, and c is the velocity of light in a vacuum.

Implicit in equation I.1 is the assumption that t is much longer than the laser pulses or the fluorescence pulses.

The duration $\Delta t$ of the pulses arriving at the photodetector is given by the expression $$\Delta t = t[(\sin \theta)^{-1} - 1] + \tau_o \text{ seconds} \qquad \text{I.2}$$

where $\theta$ is the critical angle for total internal reflection at the interface between claddings 124 and 125. In this time interval the light beam travels a distance $\Delta d$ given by $$\Delta d = n_c^{-1} \cdot c \cdot \Delta t \qquad \text{I.3}$$

This represents the minimum resolvable distance by the detector, which is assumed to have a response time no longer than the rise time of the interrogating light pulses.

An optical filter 10a allows only the fluorescence wavelengths to reach the detector.

Cladding 3 has two purposes: (a) to minimize crosstalk between the fiber core and the fluorescent cladding in the absence of an external disturbance, thereby minimizing fluorescence noise, and (b) to respond relatively strongly, due to its photoelastic properties, to an applied force, so as to "squeeze" light out of the core into the fluorescent cladding, and thus to produce a luminescence signal related in a known manner to the magnitude of said force.

Fluorescence signals are much stronger than backscattered interrogating light signals, for a given intensity of core light forced into the fluorescent cladding. Assume, for example, that the fiber has a core attenuation of 5 dB·Km$^{-1}$, and that the spatial resolution desired is 10 meters, corresponding to a time interval of $3.33 \times 10^{-8} \cdot n_c$ seconds. In this 10-meter segment, the attenuation will be 0.05 dB, of which a fraction, say, 0.03 dB, is due to scattering. Assuming that the perturbation causes a loss of 1 per cent of the core light into the cladding, then the back-scattered light $I_s$ from a 10-meter length of fiber follows the relation $$I_s = 0.67 I_p (1 - P_r) K \text{ photons·sec} \qquad \text{I.4}$$

where $I_p$ is the intensity of the interrogating light beam entering the 10-meter segment;

$P_r$ is the fraction of $I_p$ transmitted through the fiber segment, and

K is the fraction of the scattered light intensity within the acceptance angle of the fiber core.

The perturbation will produce a decrease in $I_s$ by an amount S given by $$S = 0.01 I_s \text{ photons·sec}^{-1} \qquad \text{I.5}$$

S has to be determined, of course, from the difference of the measured back-scattered light signals from two segments, one just before and the other just after the segment of interest.

The fluorescence light intensity $I_f$ generated at the cladding within the acceptance angle of the fiber and directed to the detector will be $$I_f = 0.01 I_p P_r \phi K \text{ photons·sec}^{-1} \qquad \text{I.6}$$

where $\phi$ is the luminescence quantum efficiency of the system.

It was assumed that all the light coupled out of the core into the cladding is absorbed by the fluorescent dye.

From equations I.5 and I.6 it can be determined that $$(I_f/S) = [P_r/(1 - P_r)] \phi \qquad \text{I.7}$$

The ratio $(I_f/S)$ is, therefore, approximately equal to 99 under the conditions assumed above. Thus, for a value of $\phi$ greater than 0.1, characteristic of numerous known plastic-soluble dyes, the optical signals produced by the fluorescence of the cladding can be orders of magnitude greater than the signals produced by the backscattered interrogating light. An added advantage is that they can be measured directly, free from the baseline background of the interrogating light.

In an alternate embodiment one can measure and compare the intensities of both the back-scattered interrogating light and the fluorescence light pulses. This can be done by a method similar to the one described in the following section.

J. The Use of Luminescence in Time Division Multiplexed Systems

Figure 22:
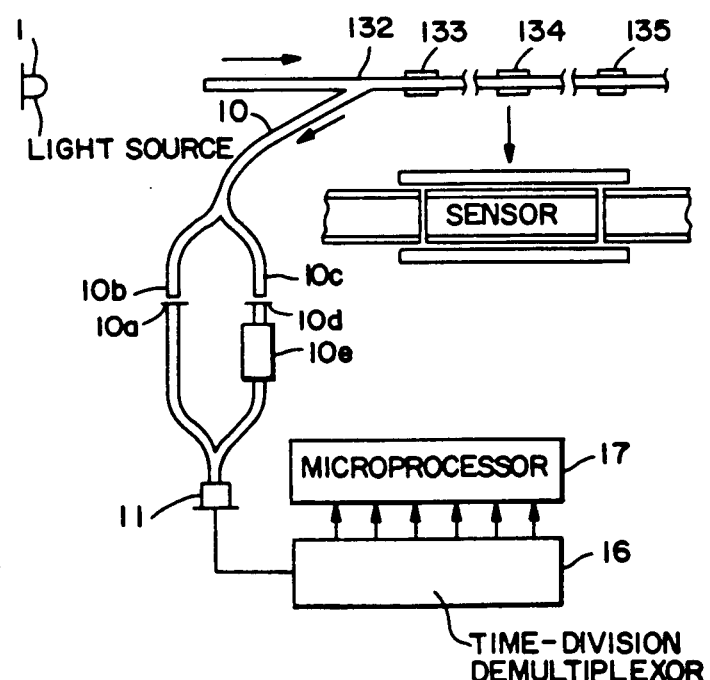
FIG. 22 shows a time division multiplexing technique according to this invention.

Luminescent sensors offer advantages compared to transmissive sensors in time division multiplexed (also known as time delay multiplexed) systems, especially at low optical densities. This can be understood with reference to FIG. 22 showing a series arrangement of a multiplicity of luminescent sensors the luminescence intensity of which is proportional to the amount of the interrogating light absorbed. A relevant example are the temperature sensors described hereinbefore.

A train of short light pulses from a laser source 1 is launched into fiber 132, having attached therein transparent sensors characterized by absorbing a small fraction of the interrogating light incident on them, said fraction being temperature-dependent. The sensors are designated by the numbers 133, 134, and 135. As the interrogating light beam (that is, the laser pulses) passes through the sensors it generates at each of them a luminescent pulse the intensity of which is proportional to the intensity of the absorbed light. A small fraction of the intensity of the laser light pulses is reflected from the face of the sensors. Both the reflected laser light pulses and the luminescent pulses travel back through fiber 132, and a fraction of their intensity is carried by fiber branch 10 to branches 10b and 10c. Optical filters 10a and 10d pass selectively the laser wavelengths and the luminescence wavelengths, respectively. A delay line 10e, which can be a chosen length of fiber, delays the luminescence pulses by a known chosen time behind the reflected laser pulses, so that they arrive at different resolved times at the photodetector 11. The photoelectric signals from the light pulses are separated by the time division demultiplexor 16. The intensity ratio of the reflected laser light and the sensor luminescence at each sensor location is measured at the microprocessor 17. The rationing process minimizes any effects from fluctuations of the intensity of the laser pulses, fiber and/or connector losses or detector drift.

It should be apparent that the optical measurements would be more susceptible to error without the ratioing process made possible by the existence of two beams of different wavelengths for each measurement. A no less important advantage is that, not only do the luminescence pulses provide a much stronger signal for the light fraction absorbed by the sensors compared to differences in backscattered or reflected light signals, but also provide a direct measurement of absorption, instead of having to determine the absorption from a small difference between two noisy signals.

Sensors which depend on changes of numerical aperture should be attached in side branches of the main fiber bus. Otherwise they would interfere with the light propagation through the bus.

K. Optical Flow Meters, Gas Pressure Meters and Liquid Level Meters

Optical Flow Meters

Gas and liquid flow meters are widely used in industry, medicine and scientific research. One of the preferred methods of measuring fluid flow is to heat a temperature sensor, in contact with the flowing fluid, to a temperature higher than that of the fluid and measure, directly or indirectly, the rate of cooling of the sensor by convection from the flowing liquid or gas. Said rate of cooling is a known function of the rate of flow.

Both the heating of the sensor and the measurement of its temperature are carried out conventionally by electrical means, the sensor being usually a thermistor or a temperature-sensitive resistor like a thin platinum film or wire.

There are situations where the use of electrical sensors is not desirable. They occur, for instance, in the presence of strong electric fields which may disturb the temperature readings, or in the presence of flammable fluids which may be accidentally ignited by the electrical conductors. In the case of physiological devices used on human patients, the introduction of current-carrying conductors into the human body carries at least the perception of hazard in a significant number of physicians.

For these reasons, there is a need for non-electrical flow meters. The meters of this invention are also based on the principle of convective cooling of a heated sensor, but in contrast to the conventional devices, both the heating of the sensor and the measurement of its temperature are accomplished entirely by optical means. The sensor is typically a material characterized by absorbing, when illuminated by light within a defined spectral region, a fraction of the intensity of said light, said fraction being a known function of the sensor temperature. Alternatively, the sensor may emit luminescence the intensity, spectral distribution or decay time of which is a known function of its temperature. Luminescent sensors offer advantages of greater sensitivity and accuracy under certain conditions, especially if spatial constraints require that both the interrogating beam and the signal beam be carried by the same fiber.

The sensor can be heated at will, directly by a beam of visible or infrared radiation of the required intensity, or indirectly by thermal conduction from an attached film which absorbs said visible or infrared radiation.

Figure 23:
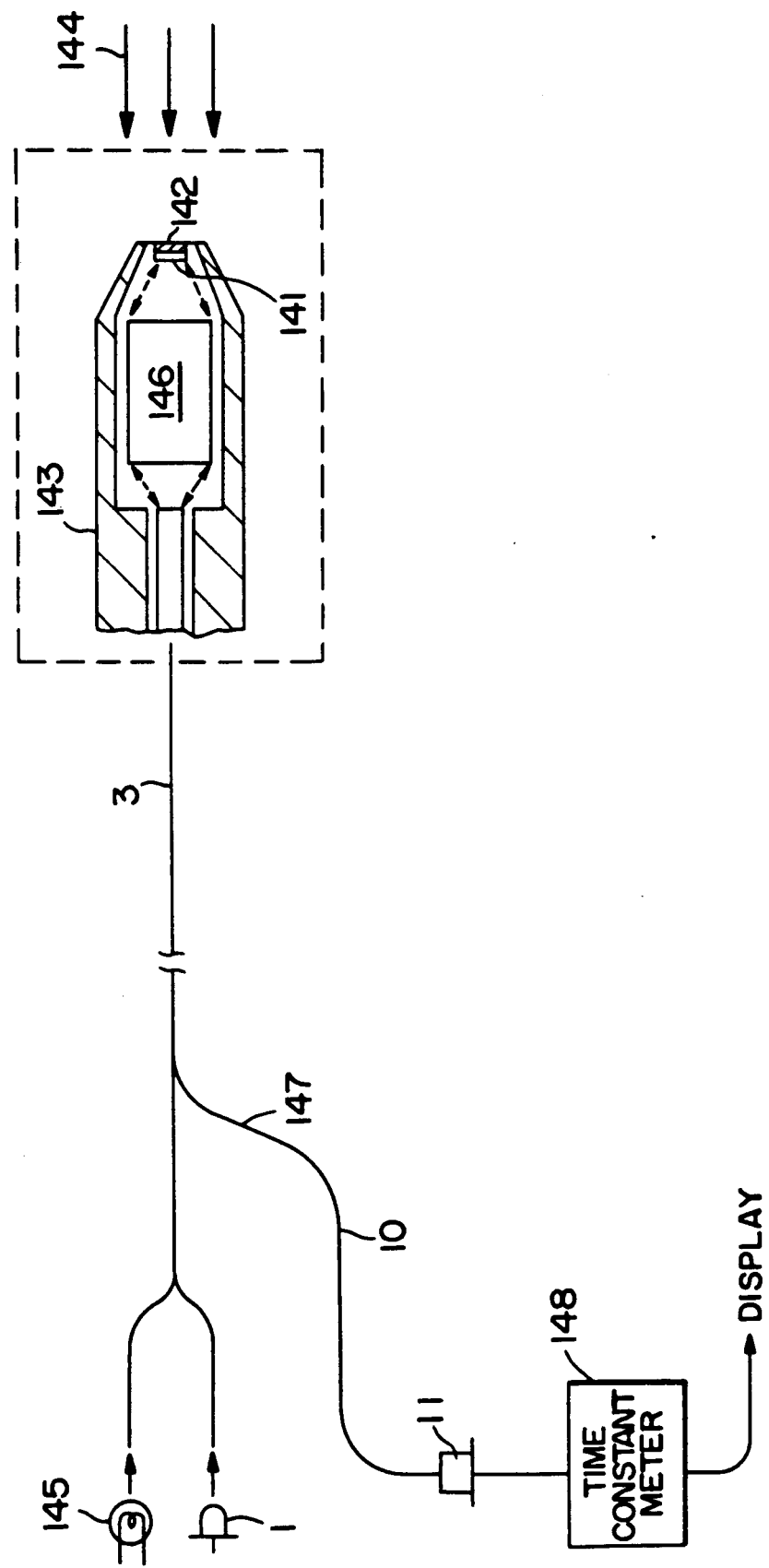
FIG. 23 shows a fiber optic flowmeter according to the invention.

An embodiment of this invention, suitable for remote measurements of gas flow, is shown in FIG. 23, explained below.

A luminescent sensor 141 in the form of a thin crystal or a microcrystalline layer is in thermal contact with a black film 142. The sensor is characterized by a temperature-dependent luminescence decay time. The bi-layered structure is contained within a holder 143, and positioned in a stream of a flowing gas 144. The sensor is heated by near infrared radiation from a source 145, via an optical fiber 3 and a cylindrical lens 146, characterized by a refractive index which decreases parabolically with the radial distance from the optical axis. Said infrared radiation is absorbed by the black layer, and the sensor is heated by thermal conduction from it to any chosen temperature higher than that of the flowing gas. The sensor temperature at any time is a known function of both the rate of heating by source 145 and the rate of convective cooling from the flowing gas, which is a known function of its rate of flow. As the rate of heating can be chosen at will, the sensor temperature is determined by the rate of gas flow being measured. The sensor temperature is measured by exciting its luminescence with pulsed light from a source 1, whereby the sensor emits luminescence pulses with a decay time which is a unique function of the sensor temperature. The sensor luminescence is isolated by optical filter 147 and carried by fiber segment 10 photo-detector 11. The photo-electric signal generated therein is fed to a time constant meter 148. The measured luminescence decay time is then an indicator of the A similar device could be used for measuring liquid flow. The rate of convective cooling of the sensor can be much higher in this case. The rate of heating of the sensor should, therefore, also be higher. Fortunately, one can transmit more than adequate power densities through silica fibers with simple sources like small incandescent lamps, light-emitting diodes (LED's) or diode lasers.

Gas Pressure Meters and Liquid Level Meters

A gas need not flow in any particular direction to withdraw heat from a heated sensor. The rate of cooling of the sensor depends in a known manner on the collision frequency of the gas molecules with the sensor, that is, on the gas pressure. Therefore, a device similar to a gas flow meter, as described above, can be used as a gas pressure gauge.

The same principles outlined above can be used for measuring liquid levels. An optical temperature sensor immersed in a liquid will clearly undergo a much lower temperature rise when heated by an optical thermal source than would the same sensor suspended in air or any other stationary gas or vapour, other things being equal.

An Optical Anemometer

Figure 24:
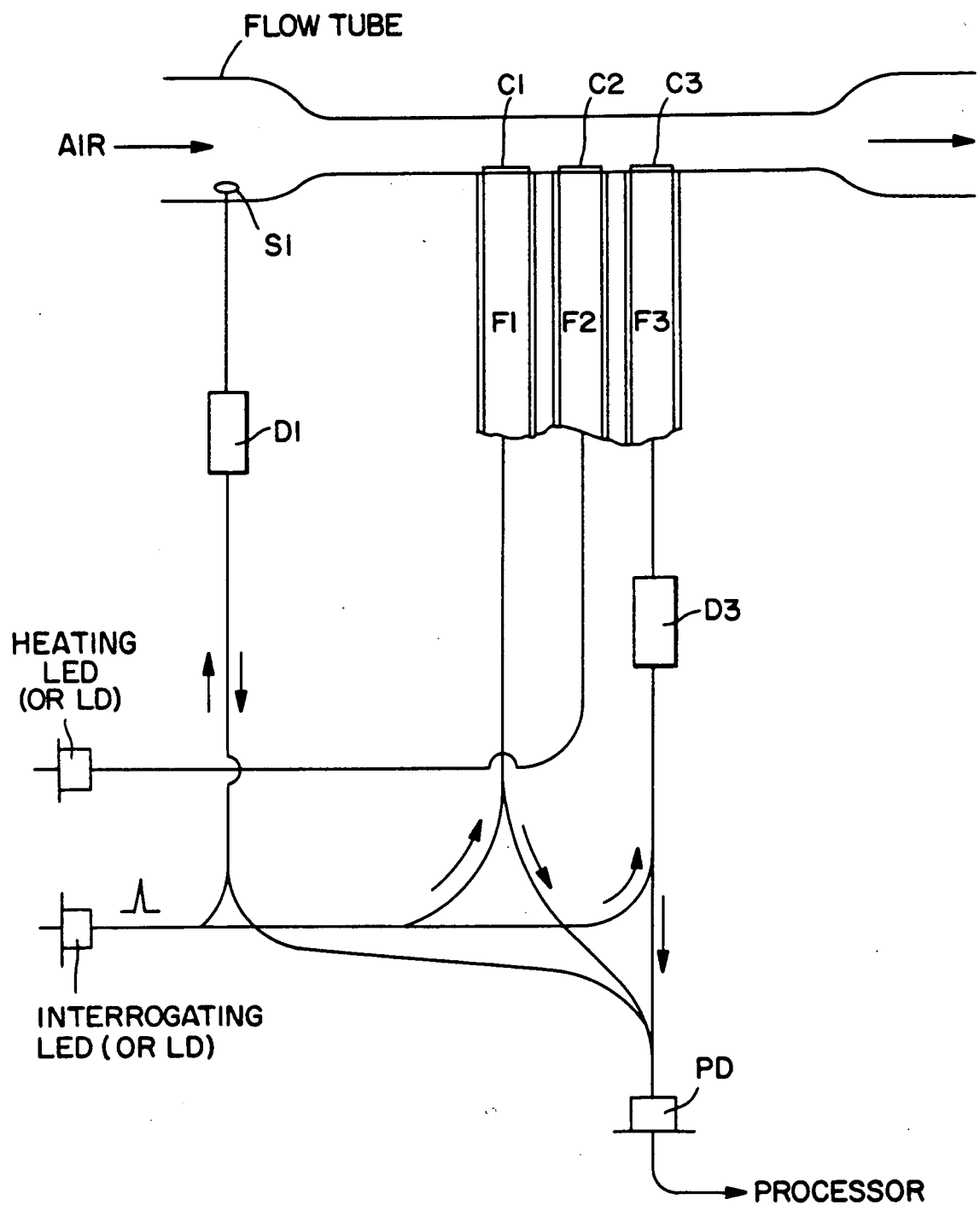
FIG. 24 shows a fiber optic analog of a thermal anemometer according to the invention.

The principle of operation of an optical thermal anemometer according to this invention can be understood with reference to FIG. 24. Three optical fibers are brought inside an air flow tube with their tips cut perpendicular to the direction of the air flow. The tip of the central fiber F2 is terminated by a "chip" C2 of material which can absorb most of the intensity of the light being directed through that fiber to the chip. Depending on the weight and thermal mass of the chip, and on the radiant energy supplied to it through the fiber, the chip can thus be heated to a temperature of tens of degrees Celsius above the temperature of the flowing air. The tips of fibers F1 and F3 are terminated in chips C1 and C3 of temperature sensors like, for instance, the ones described in Section B of this application. As air flows, for instance in the direction of the arrows, it will pick up heat from chip C2 and carry said heat to chip C3. There will be then a temperature difference $\Delta T$ between chips C1 and C3 which should obey the following relation $$\Delta T = Q_h / C_v Q_m \cdot K \text{ degrees} \qquad \text{K1}$$

where $Q_h$ is the heat input to chip C2, $C_v$ is the specific heat of the air, $Q_m$ is the air mass flow rate and $K$ is a constant.

The amount of heat that can be transferred to chip C2 by optical means is more than adequate for the temperature rise sought on chip 62. If we assume, for example, that chip C2 has a diameter of 1 mm, a specific gravity of 2.5, a thickness of 100 micrometers and a specific heat of 1.0 joules per gram per degree Celsius ($j \cdot g^{-1} \cdot \deg^{-1}$), then a heat input of 25 milliwatts should raise its temperature by more than 100 deg. Celsius under no-flow conditions.

While it is possible to produce a hot spot optically, one could heat electrically a thin film resistor by passing a measured constant current through it. To the extent that the heating is not subject to electromagnetic interference, electrical heating may be controlled more accurately than radiant heating through an optical fiber. This heating could be controlled remotely by switching on a small heating supply, like a battery, through a series photocell.

Another temperature sensor, S1, is placed some distance away from the heated segment in the flow tube, so that it will register the ambient air temperature undisturbed by the heated section.

In operation, chip C2 is heated via an optical fiber by the heating LED or laser diode LD. (As an alternative, one can use an electrically heated film or chip.) As air flows in the direction of the arrows, thereby picking up heat from C2 and producing a temperature difference $\Delta T$ between C1 and C3, these sensors (and S1) are interrogated by short (a few nanoseconds) pulses from the interrogating LED (or LD). The sensors themselves are chosen from the class of materials with a temperature-dependent absorption edge wavelength and luminescence decay times in the sub-microsecond range. They will absorb a temperature-dependent fraction of the intensity of the interrogating light pulses and emit short luminescence pulses the intensity of which defines their temperature.

Delay lines D1 and D3 are different lengths of optical fiber which delay the arrival of the interrogating light pulses to sensors S1 and C3, so that their luminescence pulses will arrive at photo-detector PD at different times in the sub-microsecond time region. Thus a single interrogating light source and a single photo-detector can measure both air flow (from the temperature difference between C1 and C2) and the ambient air temperature, so as to produce temperature-corrected readings of true wind speed.

For true wind direction one could use a plurality of flow tubes and sensors laid out in different directions. The time division multiplexing (TDM) technique described above allows the use of a single electro-optic unit with all the needed sensors.

Since certain changes may be made in the foregoing disclosure without departing from the scope of the invention herein involved, it is intended that all matter contained in the above description and depicted in the accompanying drawings be construed in an illustrative and not in a limiting sense.

What is claimed is:

1. A method for sensing variations in the magnitude of a physical parameter by use of a probe, and an interrogating light of suitable wavelength or wavelengths injected into said probe with an intensity $P_o$, comprising the steps of:

(a) exposing a light-transmitting probe to said physical parameter, said probe characterized by an ability to attenuate within said probe an interrogating light of suitable wavelength and an intensity $P_o$ entering the probe to an intensity $P_o(1-\alpha)$, where $\alpha$ is a parameter-dependent fraction smaller than unity, and to substantially convert the fraction $\alpha P_o$ of the intensity of the interrogating light into a light separable from the interrogating light, at least part of the intensity of which is emitted from the probe at wavelengths $\lambda_1$ different from the wavelength of the interrogating light.

(b) injecting into the probe interrogating light of intensity $P_o$ and of a wavelength or wavelengths within a suitable spectral region, thereby converting the fraction $\alpha P_o$ of the intensity of said injected interrogating light into emitted light at least part of the intensity of which is emitted from the probe at the wavelengths $\lambda_1$ different from the wavelength or wavelengths of the interrogating light, the value of $\alpha$ varying with the magnitude of said parameter, and said emitted light having an intensity varying with the value of $\alpha$;

(c) directing a fraction of the intensity of said emitted light to photodetector means;

(d) sensing the variations of the intensity of said emitted light received by said photodetector means, said variations being an indicator of the variations of the magnitude of the physical parameter; and (e) thereby sensing the variations in the magnitude of the physical parameter from the variations of the intensity of said emitted light received by said photodetector means.

2. The method as claimed in claim 1, additionally including the steps of:
 (a) measuring the intensity of the interrogating light transmitted by said probe; and
 (b) comparing the intensities of said interrogating light transmitted by said probe and said emitted light of wavelengths including $\lambda_1$ received by said photodetector means, their ratio being being an indicator of the magnitude of the physical parameter.

3. The method of claim 1 wherein said probe is adapted to measure temperature, and the value of $\alpha$ and the intensity of said emitted light of wavelengths including $\lambda_1$ increase in a known manner with increasing temperature.

4. The method of claim 3 wherein said wavelengths $\lambda_1$ are shorter than the wavelength or wavelengths of the interrogating light.

5. The method as claimed in claim 1 wherein said probe is an optical fiber having a substantially transparent core and a photoluminescent cladding, said interrogating light is guided along said core, said fraction $\alpha P_o$ of the intensity of the interrogating light is deflected from said core to said cladding under the influence of said parameter, and said emitted light of wavelengths including $\lambda_1$ is luminescence light generated within said cladding by said deflected light.

6. The method as claimed in claim 5 wherein the variations to be sensed modulate the magnitude of a force acting on said optical fiber, said force causing said deflection of said fraction $\alpha P_o$ of the intensity of said interrogating light from said core to said cladding.

7. The method of claim 5 adapted to measure temperature, wherein said luminescent cladding is comprised of a clear polymer containing dissolved therein a fluorescent dye and the magnitude of said fraction of the intensity of the interrogating light deflected from said core to said cladding varies as a known function of temperature.

8. The method claimed in claim 5 wherein said parameter is pressure.

9. A method as claimed in claim 5 and adapted to sense variations in the magnitude of physical forces acting at different locations, wherein said optical fiber is long enough to be laid along a path including said locations and includes a core and a fluorescent cladding, the method comprising the steps of:
 (a) laying out said optical fiber along a path which includes the locations where said forces are to be measured;
 (b) launching interrogating light pulses of submicrosecond duration into said core at the launch end of said fiber, a force-dependent fraction of the intensity of said light pulses being deflected to said fluorescent cladding at the locations along the fiber where the forces are acting, thus generating fluorescence light pulses propagating in both the forward and the backward directions along said fiber;
 (c) directing the backward-propagating fluorescence light pulses to a photodetector located near the fiber launch end; and
 (d) measuring variations of the intensities of the backward-propagating fluorescence light pulses and their times of arrival at the photodetector relative to the time of launching of the interrogating light pulses, said times of arrival being an indicator of the location along the fiber where the forces were acting, and said intensities, being an indicator of the magnitude of the forces.

10. A method as claimed in claim 1 and adapted to sense variations in the magnitude of physical parameters at a plurality of locations, wherein the sensing probe at each location is part of a series array of probes along an optical fiber pathway, and wherein the means for generating the interrogating light and the means for sensing variations of the intensity of said light of wavelengths including $\lambda_1$ emitted from each probe are part of of a time division multiplexing arrangement, the interrogating light being generated as light pulses of submicrosecond duration launched into one end of the optical fiber pathway, generating pulses of luminescence light of wavelengths including $\lambda_1$ emitted by each probe, said time division multiplexing arrangement including electronic means for measuring the times of arrival at the launch end of said fiber pathway, relative to the time of launching of the interrogating light pulses, of the pulses of light of wavelengths including $\lambda_1$ emitted by each probe, said times of arrival identifying the location of each probe.

11. A method as claimed in claim 10 wherein the sensing probes are adapted to measure temperature, each of said probes characterized by absorbing a temperature-dependent fraction of the intensity of the interrogating light incident on them, and by emitting luminescence light pulses the intensity of which is substantially proportional to the intensity of the absorbed light and increases with increasing temperature.

12. A method as claimed in claim 10 wherein said series array of probes is a continuous length of an optical fiber sensitive to said physical parameters along its length, each individual probe being a spatially resolvable segment of said continuous length at the locations where the physical parameters are being sensed.

13. A method as claimed in claim 12 wherein the physical parameters being sensed are forces, said optical fiber includes a core and a fluorescent cladding, and said forces cause the deflection of a force-dependent fraction of the intensity of the interrogating light propagating along the fiber core to the fluorescent cladding at each point under the action of a force, and the conversion of the deflected light into fluorescence light pulses.

14. A device for the optical measurement of temperature by use of a probe and an interrogating light injected into said probe, comprising
 (a) a probe so characterized that, when illuminated with interrogating light of a wavelength or wavelengths within a spectral region specific for said probe, a fraction of the intensity of said interrogating light injected into said probe is absorbed by the probe and substantially converted into luminescence light at least part of the intensity of which is emitted at wavelengths $\lambda_1$ different from the wavelength or wavelengths of the interrogating light, the value of said fraction and the intensity of said luminescence light increasing in a known manner with increasing temperature;
 (b) a source of said interrogating light;
 (c) fiber optic means for directing said interrogating light to said probe;
 (d) photodetection means adapted to measure the intensity of said emitted light of wavelengths including $\lambda_1$, (e) fiber optic means adapted to direct a fraction of the intensity of said luminescence light to said photodetection means;

15. A fiber optic thermometer, comprising:
(a) a fiber optic light guide for carrying illuminating light to an optical probe;
(b) a source of illuminating light of wavelengths within a pre-selected wavelength region;
(c) an optical probe at the end of said fiber optic light guide, said probe having a segment of optical fiber including a core and a cladding having an index of refraction lower than that of the core, the refractive index of said cladding varying as a known function of temperature within the temperature range being measured, thereby varying the intensity of the illuminating light transmitted by the probe;
(d) a photoluminescent tip terminating said probe, said tip characterized by absorbing light of wavelengths within said pre-selected wavelength region and converting it into luminescence light having different wavelengths from those of the illuminating light;
(e) a photodetector and associated electronic means for measuring the intensity of the luminescence light generated at said photoluminescent tip and collected by said optical probe, said intensity being an indicator of the index of refraction of said cladding and, hence, of the probe temperature; and
(f) fiber optic means for directing a fraction of the intensity of said luminescence light from said photoluminescent tip to said photodetector.

16. A force sensing arrangement including
(a) a relatively long force sensing optical fiber, said fiber including at least a core and a fluorescent cladding;
(b) a light source proximate to the launch end of said fiber, said light source adapted to launch interrogating light pulses of submicrosecond duration into the core of said fiber, a force-dependent fraction of the intensity of said light pulses being deflected to said fluorescent cladding at each force sensing point along the fiber, thus generating fluorescence light pulses propagating in both the forward and the backward directions along said fiber, the times of arrival at the fiber launch end of the backward-propagating light pulses relative to the times of launching of the interrogating light pulses identifying the locations along the fiber of each sensing point; and
(c) a photodetector and associated electronic means located near the launch end of said fiber for receiving the backward-propagating fluorescence light pulses generated at each sensing point along the fiber and for processing said fluorescence light pulses into force distributions along the fiber.

17. A fiber optic device adapted to sense variations in the magnitude of a physical parameter, including
(a) a light-transmitting probe so characterized that, when exposed to the physical parameter and transmitting interrogating light of a wavelength or wavelengths suitable for said probe and an intensity $P_o$ injected into the probe, a fraction $\alpha P_o$ of the intensity of said injected light is converted within said probe into a light separable from the interrogating light, at least part of the intensity of which is emitted from the probe at wavelengths $\lambda_1$ different from the wavelength or wavelengths of the interrogating light, the value of $\alpha$ varying in a known manner with the magnitude of the physical parameter, said emitted light of wavelengths $\lambda_1$ having an intensity which increases in a known manner with the value of $\alpha$;
(b) means for generating said interrogating light;
(c) fiber optic means for directing said interrogating light to said probe;
(d) fiber optic means for directing part of the intensity of said converted light of wavelengths including $\lambda_1$ to photodetector means; and
(e) photodetector and associated electronic means for processing said light 18. A device as claimed in claim 17 wherein said probe is an optical fiber.

19. A device as claimed in claim 18 wherein said probe is an optical fiber comprising a transparent core into which the interrogating light is injected and a cladding, said cladding having a photoluminescent material dissolved therein, said probe so characterized that, when exposed to the physical parameter being sensed and transmitting said interrogating light injected into the fiber core, a fraction of the intensity of the interrogating light propagating along said core is deflected into said cladding and converted into luminescence light, the magnitude of said fraction and the intensity of said luminescence light varying with the magnitude of the physical parameter.

20. A device as claimed in claim 19 wherein said optical fiber is adapted to sense physical forces acting on it.

21. A device as claimed in claim 17 wherein said device operates within a range of magnitudes of said parameter and said fraction $\alpha P_o$ of the intensity of the interrogating light is absorbed by a photoluminescent material within the probe and thereby converted into luminescence light, most of the intensity of which is emitted at wavelengths different from the wavelength or wavelengths of the interrogating light, the luminescence quantum efficiency, spectral distribution and decay time of said photoluminescent material not varying substantially as the magnitude of the physical parameter varies within the range of magnitudes within which the device operates.

22. A device as claimed in claim 21 wherein said emitted light of wavelengths including $\lambda_1$ is fluorescence light, said probe is part of a series array of probes along an optical fiber pathway, the interrogating light and said photodetector means are part of an electro-optical time division multiplexing arrangement optically connected to one end of said pathway, the interrogating light is generated as light pulses of submicrosecond duration injected into said one end, the fluorescence light is emitted from said probes of the array as pulses of submicrosecond duration, and part of the intensity of said emitted light is backward-propagated toward said one end of said pathway, said arrangement including opto-electronic means for measuring the time of arrival at said one end, relative to the time of injection of the interrogating light pulses, of said fluorescence light pulses, said time of arrival identifying the location of said probes along the array.

23. A device as claimed in claim 22 wherein said series array of probes is a long continuous optical fiber sensitive to variations of said physical parameter along its length, each of said probes being a spatially resolvable segment of said continuous fiber at a location along the fiber where the physical parameter is being sensed.

24. A device as claimed in claim 17 and additionally comprising:
(a) means for directing at least a fraction of the intensity of the unconverted light transmitted by said probe to photodetector means and for measuring the intensity of said transmitted unconverted light received by said photodetector means; and
(b) electronic means for deriving the magnitude of the physical parameter from the measured relative intensities of said converted light including wavelengths $\lambda_1$ emitted by the probe and said unconverted interrogating light transmitted by the probe.

25. A device as claimed in claim 17 wherein said probe is a temperature probe, and the value of $\alpha$ and the intensity of said emitted light of wavelengths including $\lambda_1$ increase with increasing temperature.

26. A device as claimed in claim 25 wherein said wavelengths $\lambda_1$ of the emitted light are shorter than the wavelength or wavelengths of the interrogating light.

27. A temperature measuring arrangement comprising an optical probe doped with material that luminesces in response to the absorption of light in dependence upon temperature, means for injecting interrogating light into said probe and means for detecting variations in the levels of luminescence light which is emitted by the doped material in response to variations in the absorption of the interrogating light, wherein the intensity of the luminescence light emitted from the probe is indicative of the temperature of the probe.

28. A temperature measuring arrangement as claimed in claim 27 wherein said absorption of light and the intensity of said luminescence light increase with increasing temperature.

* * * * *